US010406228B2

(12) United States Patent
Ivkov

(10) Patent No.: US 10,406,228 B2
(45) Date of Patent: Sep. 10, 2019

(54) PROCESS FOR MAKING IRON OXIDE NANOPARTICLE PREPARATIONS FOR CANCER HYPERTHERMIA

(71) Applicant: THE JOHNS HOPKINS UNIVERSITY, Baltimore, MD (US)

(72) Inventor: Robert Ivkov, Ellicott City, MD (US)

(73) Assignee: THE JOHNS HOPKINS UNIVERSITY, Baltimore, MD (US)

(*) Notice: Subject to any disclaimer, the term of this patent is extended or adjusted under 35 U.S.C. 154(b) by 217 days.

(21) Appl. No.: 14/648,080

(22) PCT Filed: Nov. 27, 2013

(86) PCT No.: PCT/US2013/072328
§ 371 (c)(1),
(2) Date: May 28, 2015

(87) PCT Pub. No.: WO2014/085651
PCT Pub. Date: Jun. 5, 2014

(65) Prior Publication Data
US 2015/0320862 A1  Nov. 12, 2015

Related U.S. Application Data

(60) Provisional application No. 61/793,871, filed on Mar. 15, 2013, provisional application No. 61/731,192, filed on Nov. 29, 2012.

(51) Int. Cl.
*A61K 41/00* (2006.01)
*C01G 49/08* (2006.01)
(Continued)

(52) U.S. Cl.
CPC ........ *A61K 41/0052* (2013.01); *A61K 9/5015* (2013.01); *A61K 9/5089* (2013.01); *A61K 9/5115* (2013.01); *A61K 9/5192* (2013.01); *A61K 33/00* (2013.01); *A61K 33/26* (2013.01); *A61N 2/004* (2013.01); *A61N 2/02* (2013.01); *C01G 49/06* (2013.01); *C01G 49/08* (2013.01); *C01P 2002/72* (2013.01); *C01P 2004/03* (2013.01); *C01P 2004/04* (2013.01); *C01P 2004/51* (2013.01); *C01P 2004/64* (2013.01);
(Continued)

(58) Field of Classification Search
CPC .. A61K 9/5115; A61K 41/0052; A61N 2/004; C01G 49/08
See application file for complete search history.

(56) References Cited

U.S. PATENT DOCUMENTS 4,822,509 A  4/1989  Bishara
7,615,096 B1  11/2009  Tai
(Continued)

OTHER PUBLICATIONS

Atkinson, W.J., Brezovich, I.A., Chakraborty, D.P., "Usable frequencies in hyperthermia with thermal seeds," IEEE Trans. Biomed. Eng. 31,70-75 (1984).
(Continued)

*Primary Examiner* — Thaddeus B Cox
(74) *Attorney, Agent, or Firm* — Casimir Jones, S.C.; Jeffrey W. Childers

(57) ABSTRACT

Iron oxide nanoparticle compositions, methods of preparing the nanoparticles using high gravity controlled precipitation (HGCP), and methods of using the nanoparticles are disclosed.

2 Claims, 32 Drawing Sheets

(51) Int. Cl.
*A61N 2/02* (2006.01)
*A61K 9/51* (2006.01)
*A61K 9/50* (2006.01)
*A61N 2/00* (2006.01)
*A61K 33/26* (2006.01)
*C01G 49/06* (2006.01)
*A61K 33/00* (2006.01)

(52) U.S. Cl.
CPC ...... *C01P 2004/84* (2013.01); *C01P 2006/90* (2013.01)

(56) References Cited

U.S. PATENT DOCUMENTS

| 7,985,388 | B2 | 7/2011 | Shen | |
| 2006/0142749 | A1* | 6/2006 | Ivkov | A61K 41/0052 606/27 |
| 2010/0298123 | A1 | 11/2010 | Shen | |
| 2011/0223255 | A1* | 9/2011 | Thiesen | A61K 9/0024 424/489 |
| 2012/0277517 | A1 | 11/2012 | Ivkov | |

OTHER PUBLICATIONS

Black, D.R., [Thermoregulation in the presence of radio frequency fields], Biological and Medical Aspects of Electromagnetic Fields, 3rd Edition, Boca Raton, 215-226 (2006).
Bordelon, D., et al. "Magnetic nanoparticle heating efficiency reveals magneto-structural differences when characterized with wide ranging and high amplitude alternating magnetic fields," Journal of Applied Physics 109,12904.1-12904.8 (2011).
Bordelon, D., Goldstein, R., Nemkov, V., Kumar, A., Jackowski, J., DeWeese, T.L., Ivkov, R., "Modified solenoid coil that efficiently produces high amplitude AC magnetic fields with enhanced uniformity for biomedical applications," IEEE Trans. on Magnetics 48,47-52 (2012).
Dennis C.L., A.J. Jackson, J.A. Borchers, P.J. Hoopes, R. Strawbridge, A.R. Foreman, J. van Lierop, C. Griittner, and R. Ivkov, Nanotechnology, 20 (2009) 395103.
Gruettner C, K. Mueller, J. Teller, F. Westphal, A. Foreman, and R. Ivkov, J. "Synthesis and antibody conjugation of magnetic nanoparticles with improved specific power absorption rates for alternating magnetic field cancer therapy," Journal of Magnetism and Magnetic Materials 311(1), 181-186 (2007).
Kim, J., J.E. Lee, S.H. Lee, J.H. Yu, J.H. Lee, T.G. Park, and T. Hyeon, Adv.Mater., 20 (2008) 478.
Taketomi, S. and R.D. Shull, J. Appl. Phys., 91 (2002) 8546-8548.
Repetto G, et al. "Neutral red uptake assay for the estimation of cell viability/cytotoxicity," Nature Protocols 3(7), 1125-1131 (2008).
Krycka, K. L., A.J. Jackson, J.A. Borchers, J. Shih, R. Briber, R. Ivkov, C. Griittner, and C.L. Dennis, Journal of Applied Physics, 109 (2011) 07B513.
Nemkov V, et al. "Magnetic field generating inductor for cancer hyperthermia research," Compel 10(5),1626-1636 (2011).
Poddar, P., M.B. Morales, N. A. Frey, S.A. Morrison, E.E. Carpenter, and H. Srikanth, J. Appl. Phys., 104 (2008).
International Search Report dated Mar. 27, 2014 from PCT International Application No. PCT/US2013/72328.

* cited by examiner

PC3 CELLS WITHOUT PARTICLES (LEFT) AND AFTER EXPOSURE TO PARTICLES (RIGHT)

PROCESS FOR MAKING IRON OXIDE NANOPARTICLE PREPARATIONS FOR CANCER HYPERTHERMIA

CROSS REFERENCE TO RELATED APPLICATIONS

This application is a 35 U.S.C. § 371 National Stage Entry of International Application No. PCT/US2013/72328 having an international filing date of Nov. 27, 2013, which claims the benefit of U.S. Provisional Application No. 61/793,871, filed Mar. 15, 2013, and U.S. Provisional Application No. 61/731,192, filed Nov. 29, 2012, the content of each of the aforementioned applications is herein incorporated by reference in its entirety.

BACKGROUND

Despite the great promise, magnetic nanoparticle hyperthermia (mNHP) has had limited success in clinical applications. This limited success is due, in part, to technical difficulties of selective heat delivery to the target tissue without overheating adjacent normal tissue. Magnetic nanoparticle hyperthermia for cancer therapy is an application of alternating magnetic fields (AMFs) in which magnetic nanoparticle heating depends upon both AMF frequency and amplitude (Jordan et al., 1997; Rosensweig, 2002; Bordelon et al., 2011). Generally, the objective is to develop nanoparticle and AMF device combinations that produce a maximum particle-associated heating rate, or loss power for a given flux (peak-to-peak) magnetic field. For many magnetic materials, the loss power increases both with increasing AMF frequency and amplitude, thus motivating development of particles that generate therapeutic heating with safe AMF exposure. For a given magnetic ion oxide nanoparticle (MION) formulation localized in tissue, the amount of heat deposited during mNHP depends on both the intratumoral iron-oxide nanoparticle (IONP) concentration and AMF parameters.

When a region of tissue in an animal or a patient is subjected to alternating magnetic field (AMF), non-specific Joule heat is deposited into the tissue due to eddy currents. The total non-specific power deposited is proportional to $H^2f^2r^2$; where H and f are AMF amplitude and frequency, and r is the radius of the eddy current path, which is related to the radius of tissue exposed to AMF. For most iron-oxide nanoparticles (IONPs) the heat generating ability is proportional to $H^2f$ Hence, lower AMF frequencies in the range of 100 kHz to 400 kHz are typically used in mNPH applications (Atkinson et al., 1984). For mNPH to be effective, the IONPs should generate higher heating at low field amplitude, or H-values.

SUMMARY

In some aspects, the presently disclosed subject matter provides a process for preparing one or more surfactant-coated magnetic metal oxide particles, the process comprising: (a) providing a salt solution of a metal; (b) contacting the salt solution of the metal with a precipitant solution to form a reactant solution; (c) rapidly micro-mixing the reactant solution to initiate formation of metal oxide crystals under controlled nucleation conditions; (d) continuing to rapidly micro-mix the reactant solution under high gravity conditions to control crystal growth of one or more metal oxide particles formed therein; (e) coating the one or more metal oxide particles with a surfactant; (f) separating the one or more coated metal oxide particles from the reactant solution and one or more by-products, if present, formed therein; and (g) exposing the one or more coated metal oxide particles to high temperature and high pressure in an inert gas environment for a period of time to form one or more surfactant-coated magnetic metal oxide particles.

In other aspects, the presently disclosed subject matter provides one or more surfactant-coated magnetic metal oxide particles prepared by the presently disclosed methods.

In more particular aspects, the presently disclosed subject matter provides a magnetic metal oxide nanoparticle prepared from a high-gravity controlled precipitation reaction, the nanoparticle comprising: (a) iron oxide crystals having a dimension ranging from about 5 nm to about 100 nm; and (b) a surfactant coating; wherein the nanoparticle has a heating property of greater than about 60 W/g Fe in an alternating current (AC) magnetic field having a frequency of ranging from about 50 kHz and to about 1 MHz and an amplitude ranging from about 0.080 kA/m to about 50 kA/m. In yet more particular aspects, the nanoparticle comprises about 76% $Fe_3O_4$ and about 24% $\gamma$-$Fe_2O_3$ and is substantially free of $Fe(OH)_2$.

In yet other aspects, the presently disclosed subject matter provides a biocompatible suspension comprising a magnetic metal oxide nanoparticle prepared by a high-gravity controlled precipitation reaction and water.

In further aspects, the presently disclosed subject matter provides a method for treating a diseased tissue, the method comprising: (a) administering to a tissue or a subject in need of treatment thereof, a therapeutically effective amount of a magnetic nanoparticle comprising surfactant-coated iron oxide crystals prepared from a high-gravity controlled precipitation process; and (b) subjecting the tissue or subject, or a portion of the tissue or subject to an alternating current (AC) magnetic field having frequency ranging from about 50 kHz to about 1 MHz and having an amplitude (peak-to-peak) ranging from about 0.080 kA/m to about 50 kA/m. In particular aspects, the diseased tissue comprises a cancer tissue.

In yet further aspects, the presently disclosed subject matter provides a magnetic nanoparticle comprising: (a) a magnetic core comprising an aggregate of at least two magnetic crystalline grains, wherein the aggregate exhibits a collective magnetic phase such that the core has an apparently single magnetic domain phase; (b) a second magnetic phase or magnetic oxide phase differing from the collective or single domain phase of the core, wherein the second magnetic phase or magnetic oxide phase can intercalate and surround the core; wherein at least one magnetic phase exhibits a "hard" or high-coercive behavior in a magnetic field and at least one other phase exhibits a "soft" or low-coercive behavior in a magnetic field relative to the "hard" magnetic phase; and (c) a coating. In particular aspects, the core substantially comprises $Fe_3O_4$ and the second magnetic phase or magnetic oxide phase substantially comprises $\gamma$-$Fe_2O_3$.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
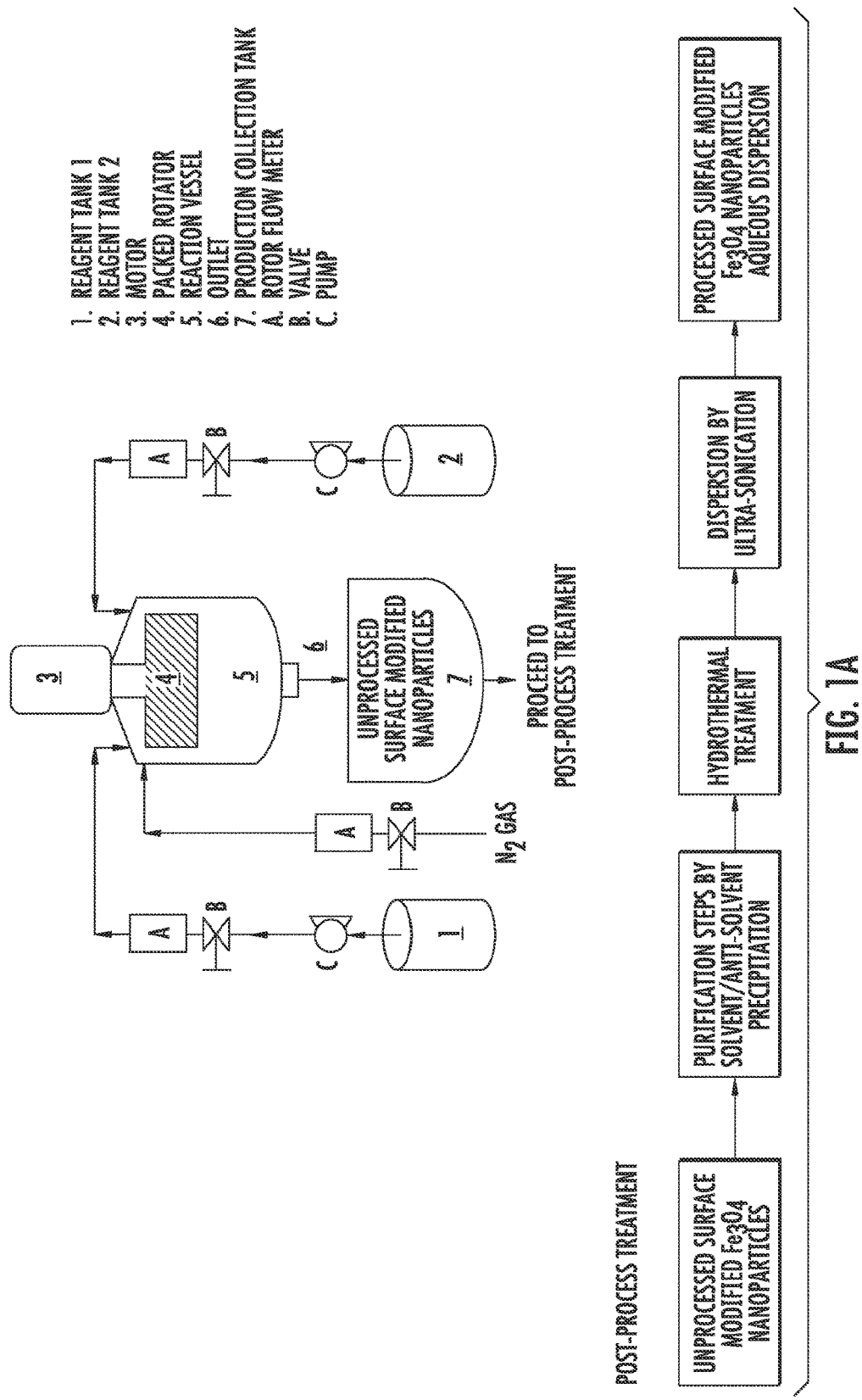
Figure 1B:
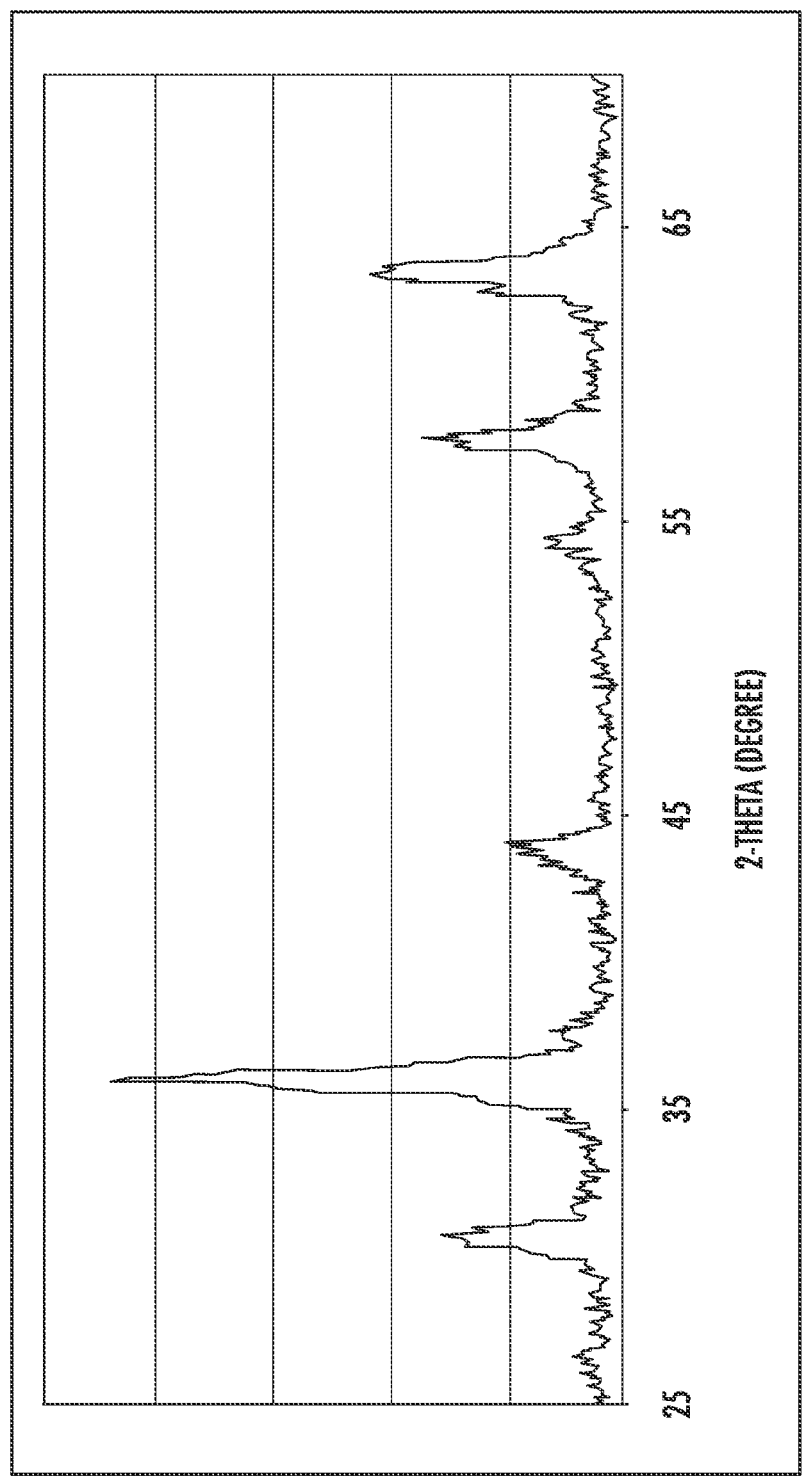
Figure 2A:
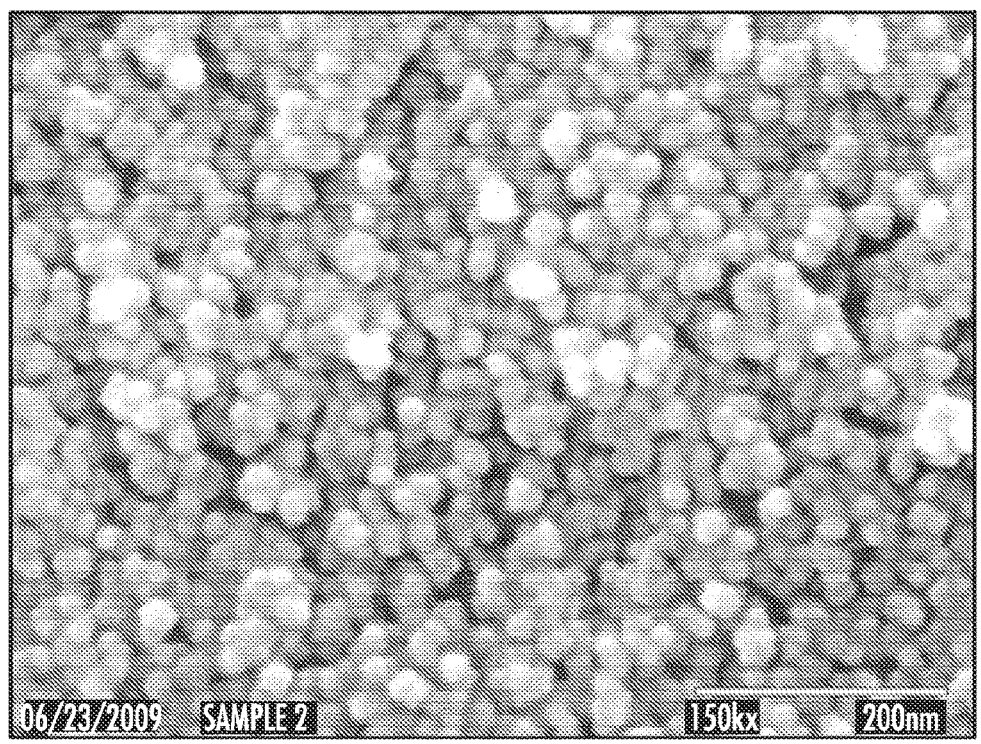
Figure 2B:
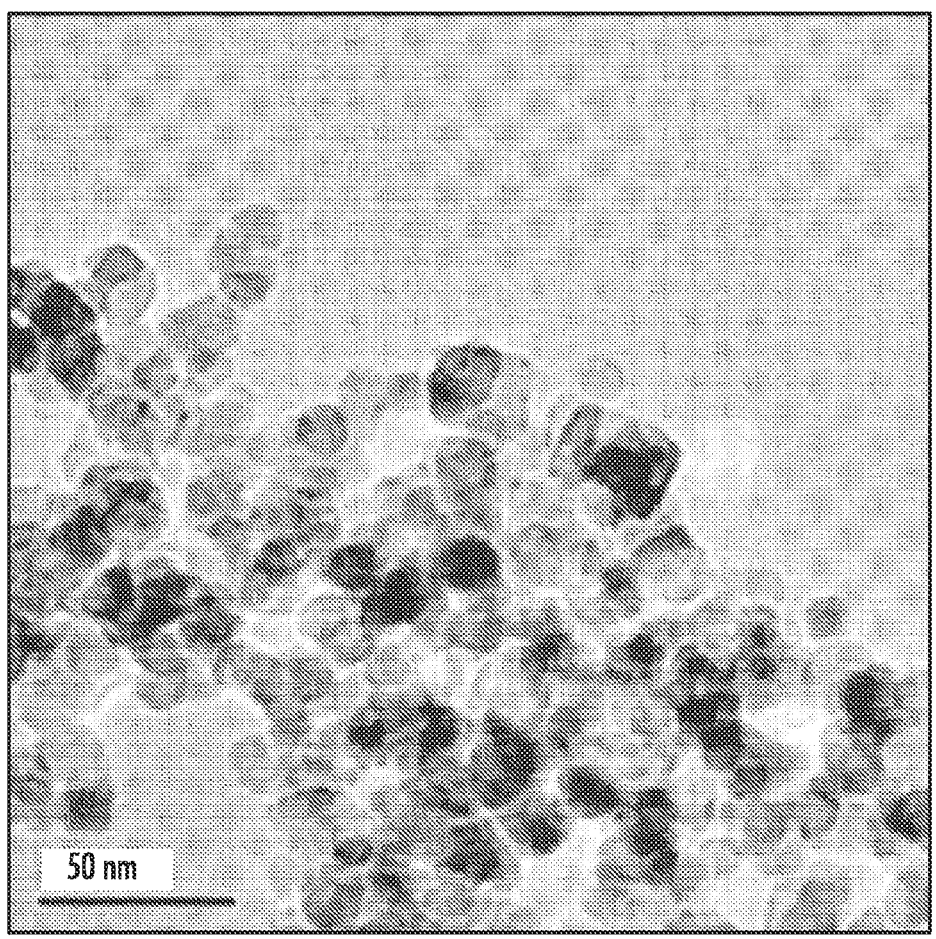
Figure 2C:
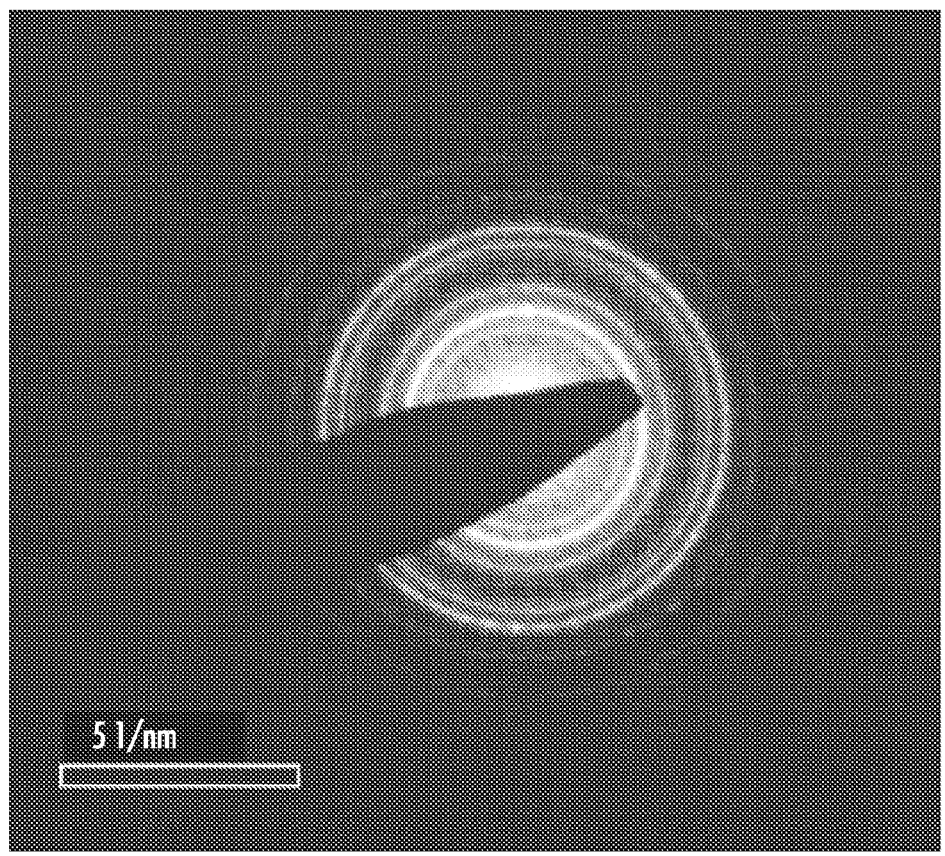
Figure 3A:
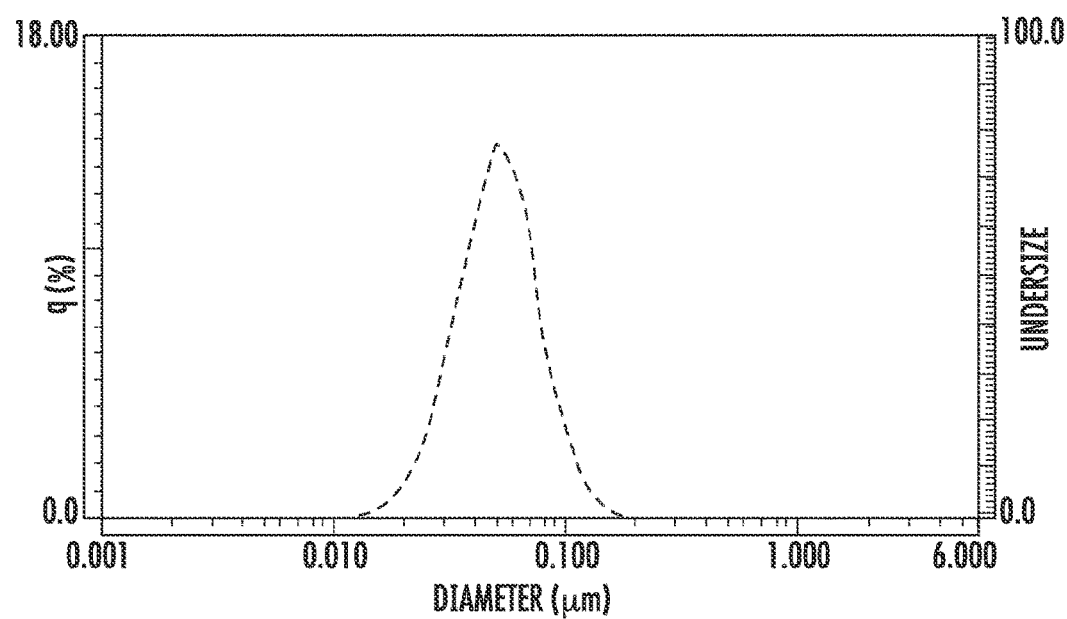
Figure 3B:
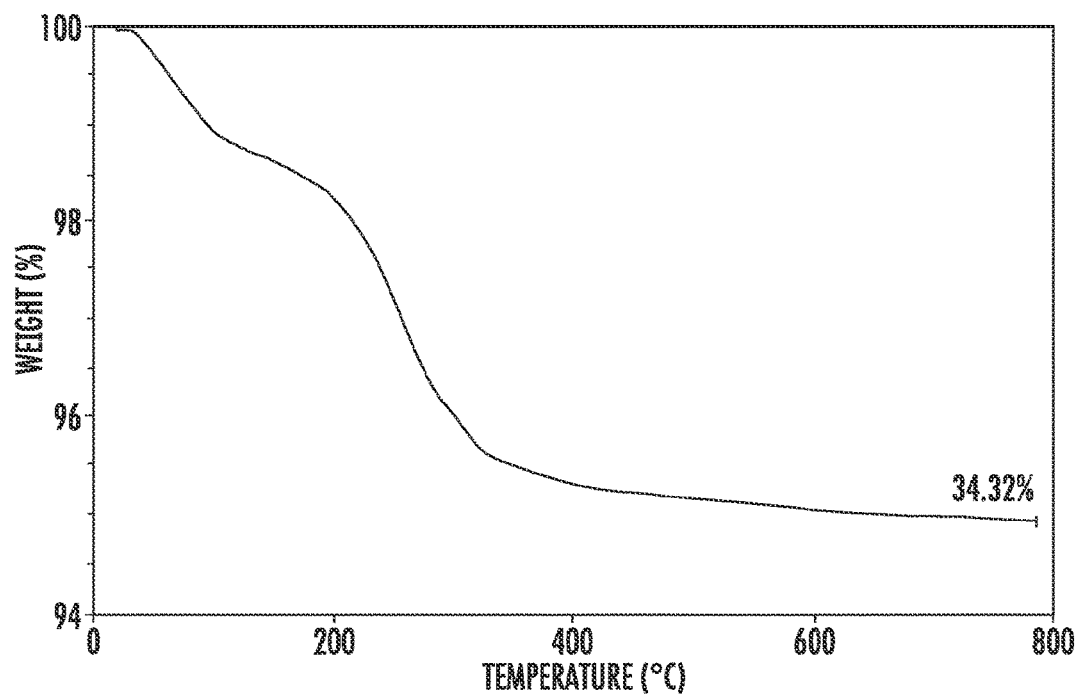
Figure 3C:
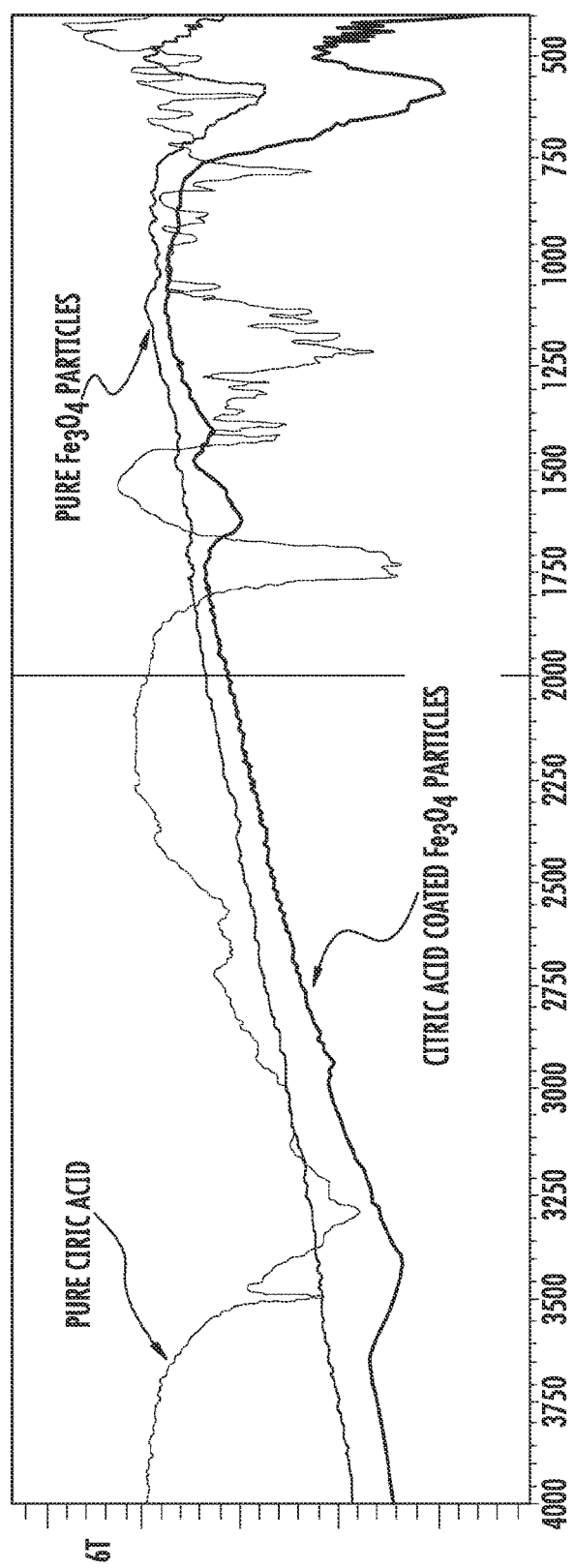
Figure 4:
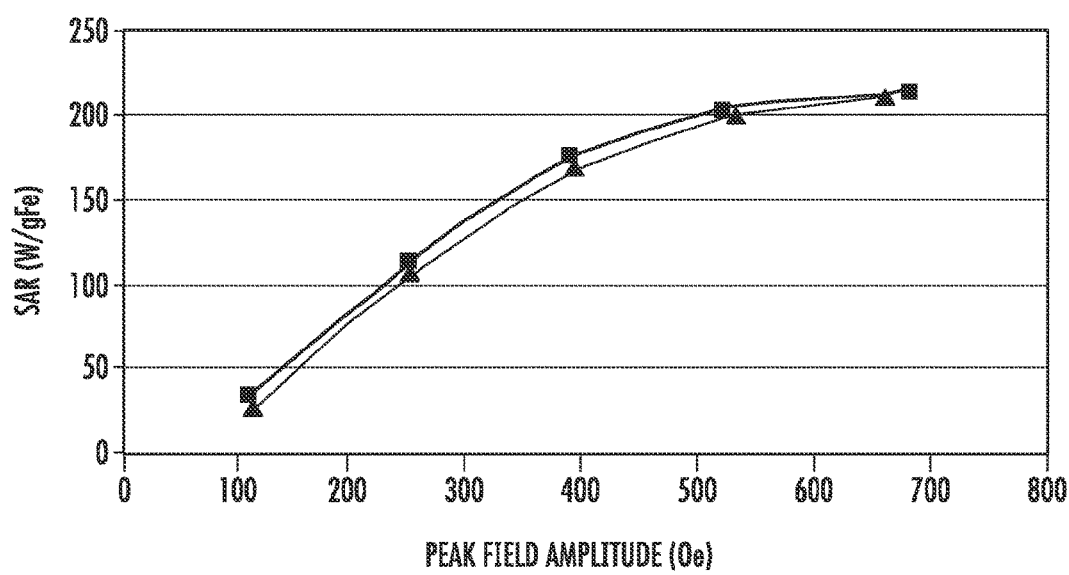
Figure 5A:
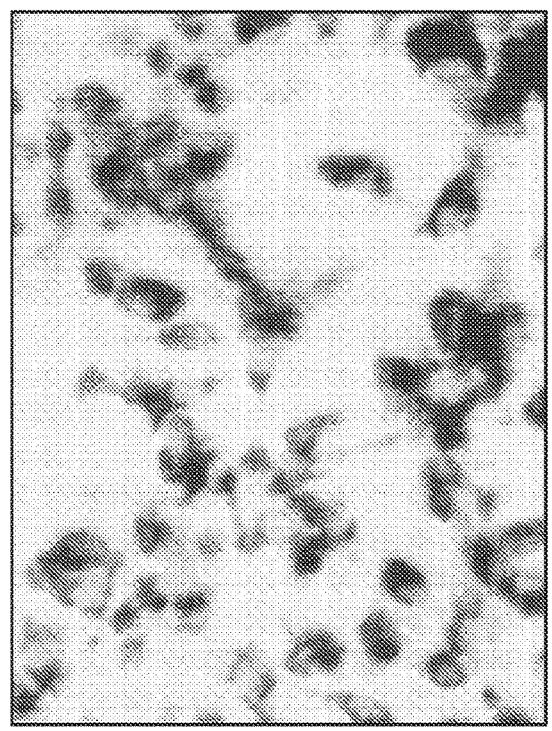
Figure 5A:
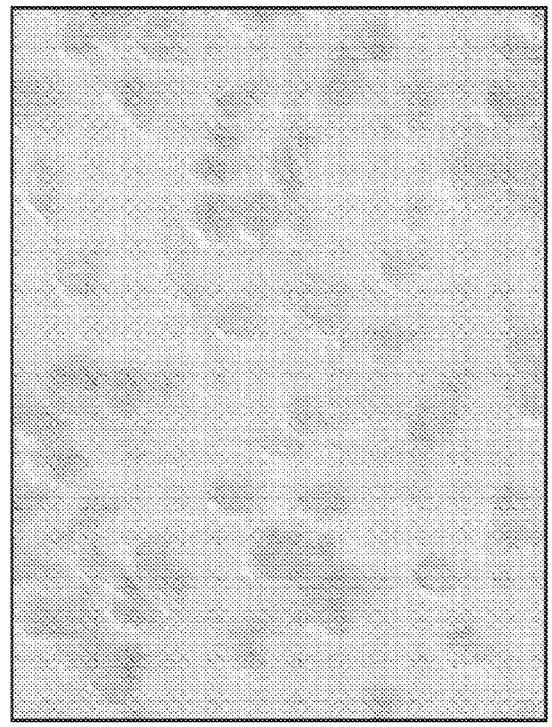
Figure 5B:
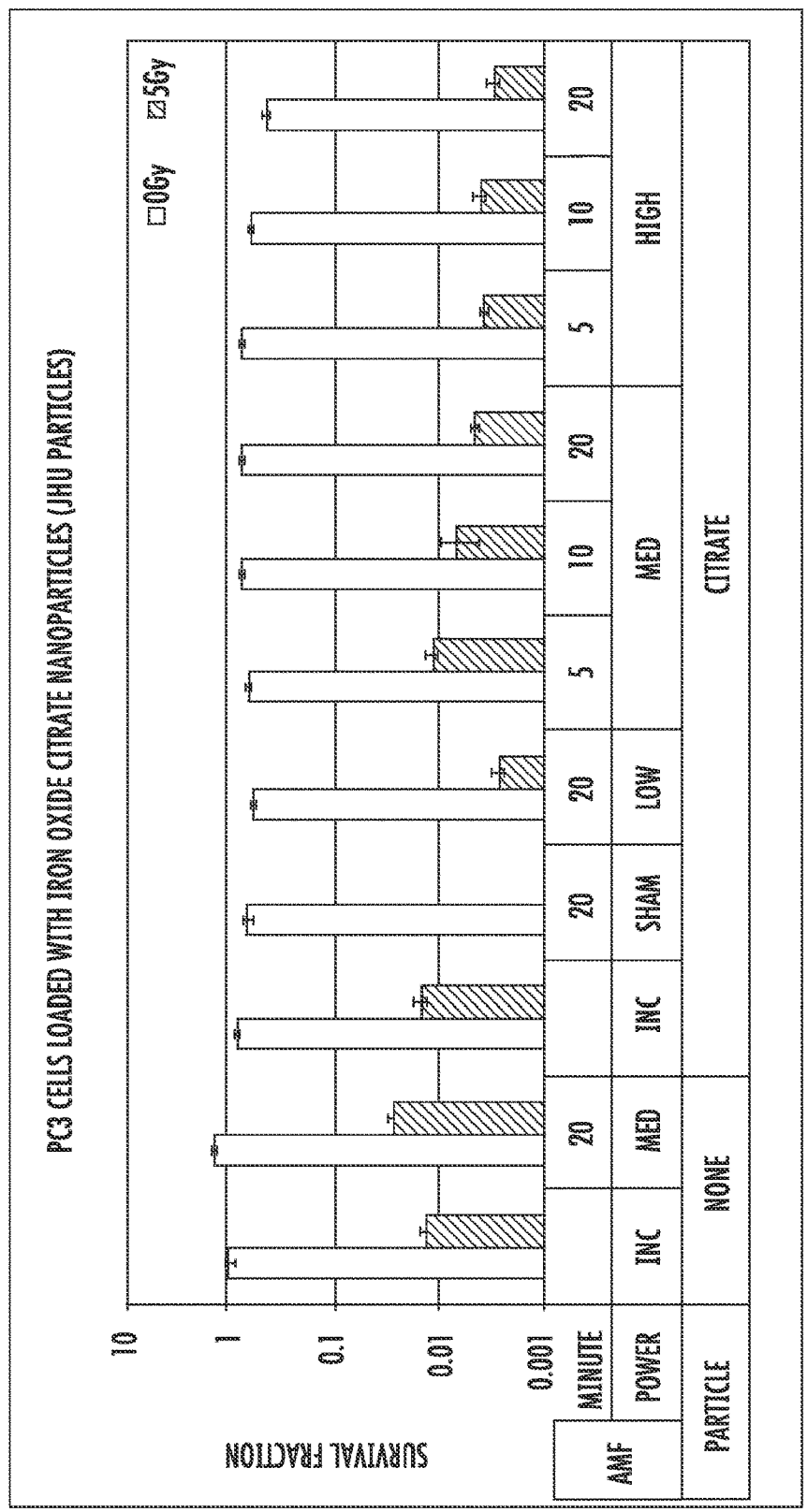
Figure 5C:
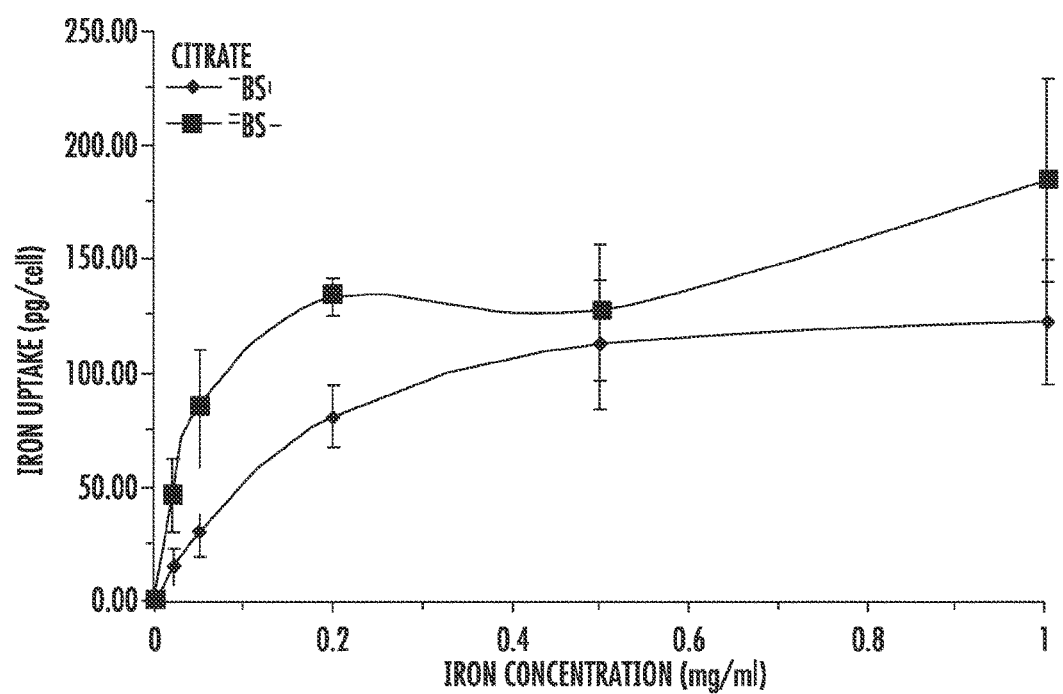
Figure 6:
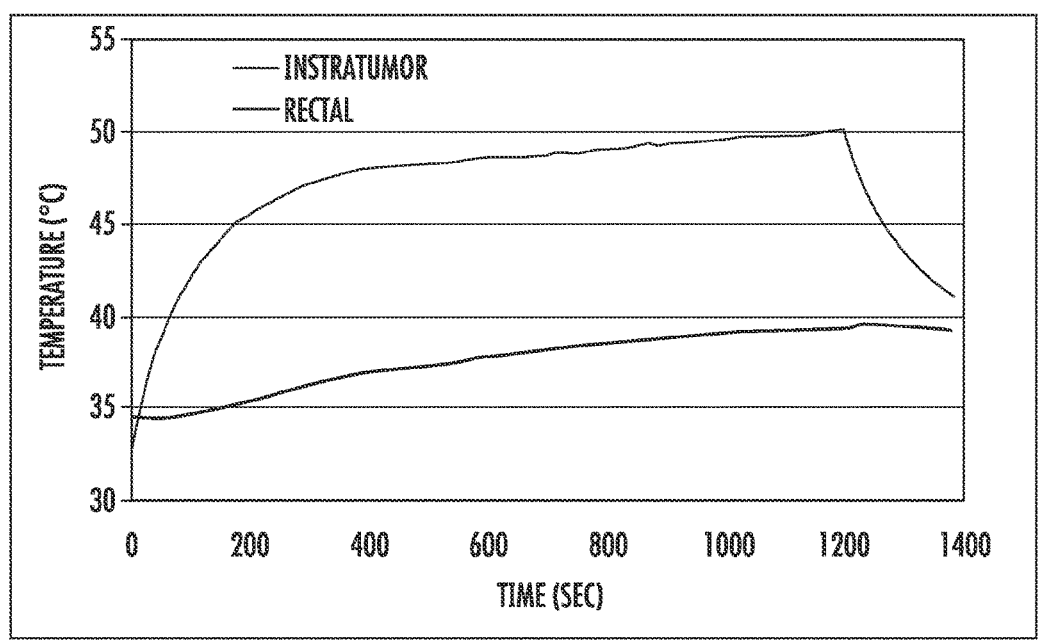
Figure 7:
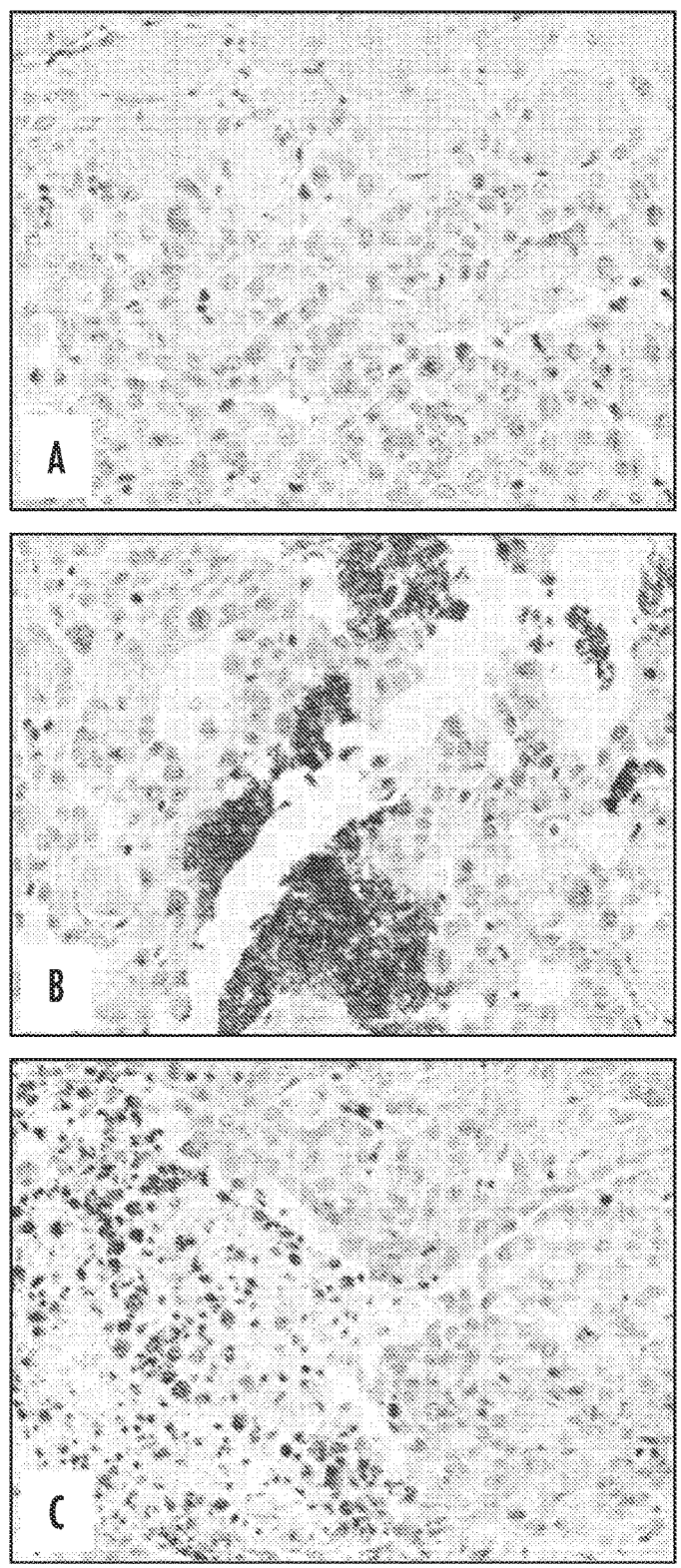
Figure 8B:
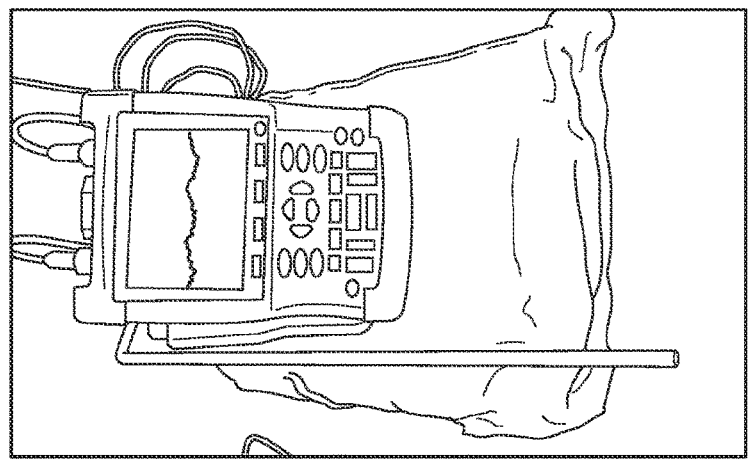
Figure 8A:
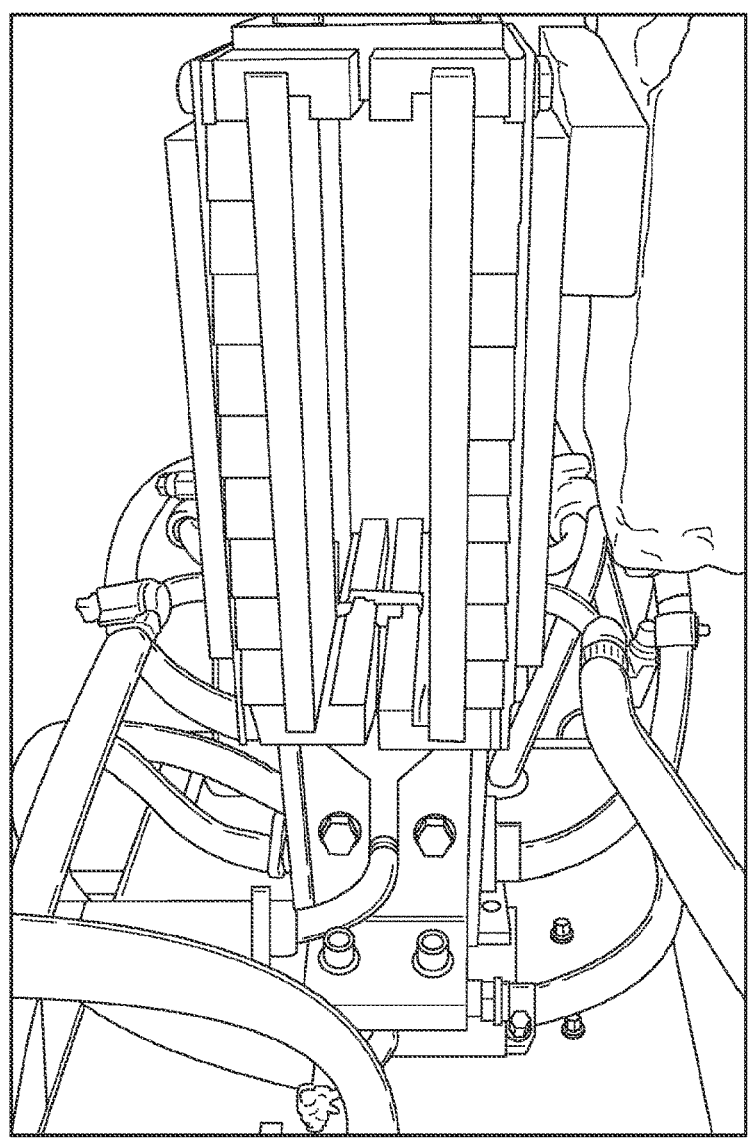
Figure 9:
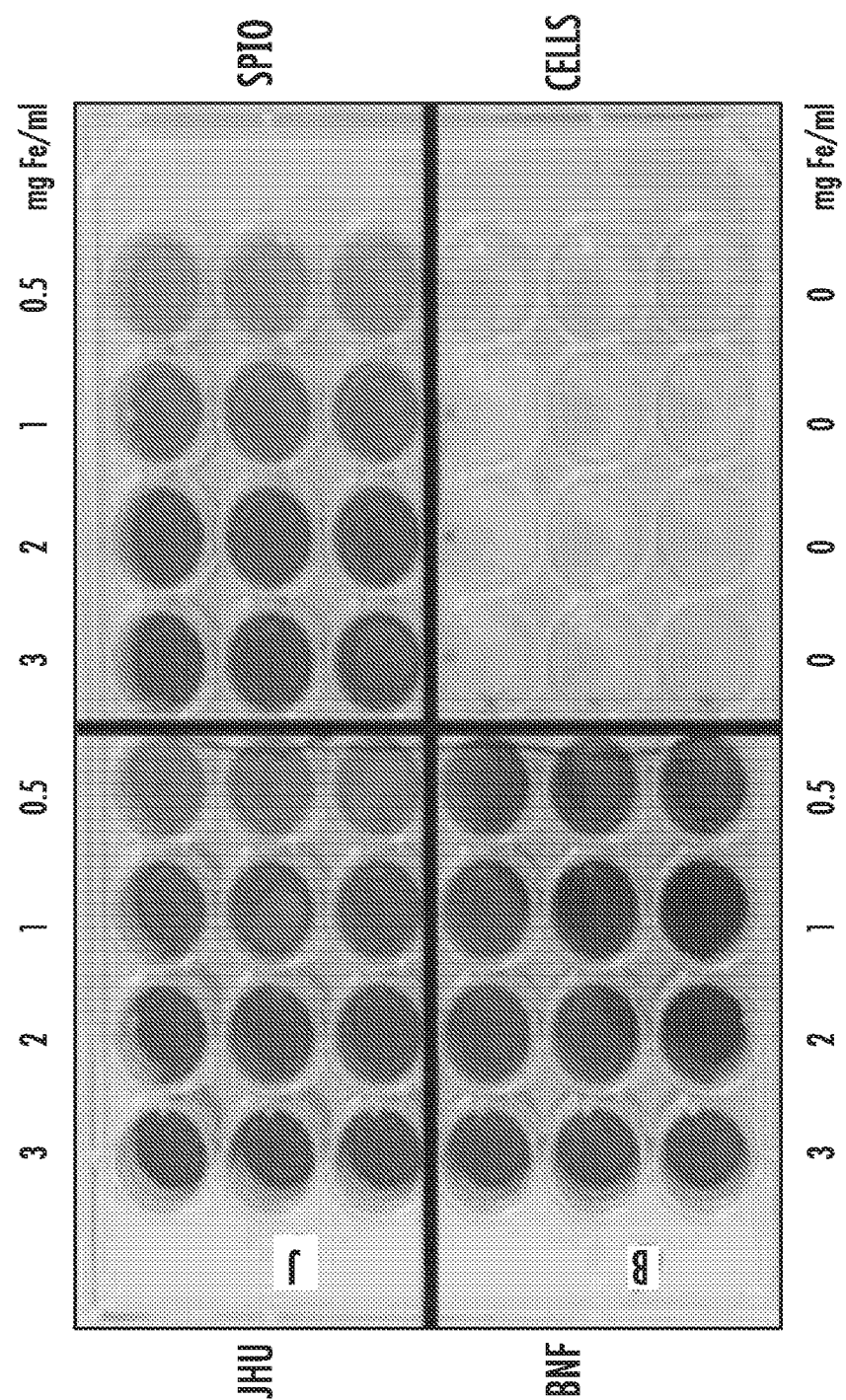
Figure 10:
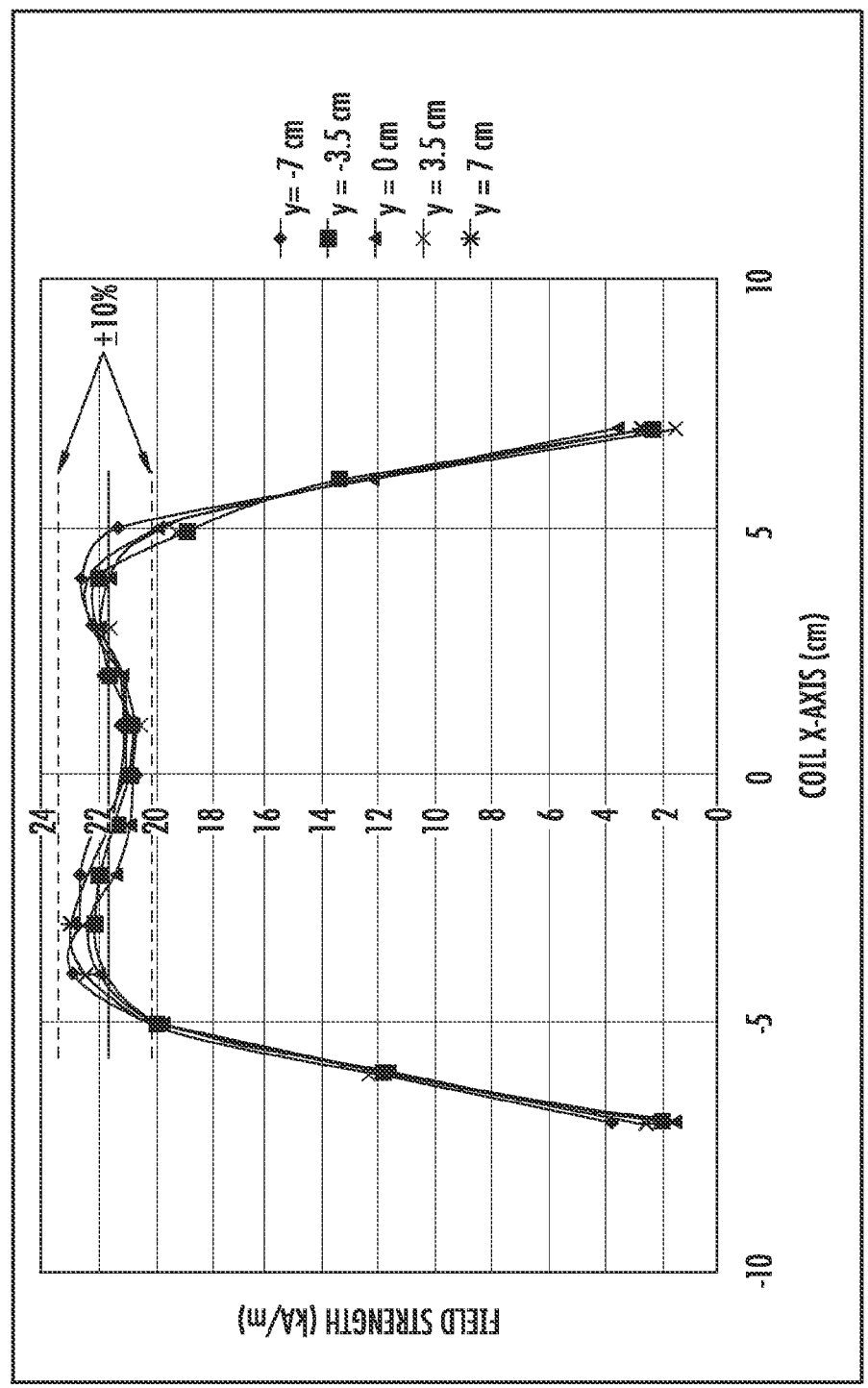
Figure 11:
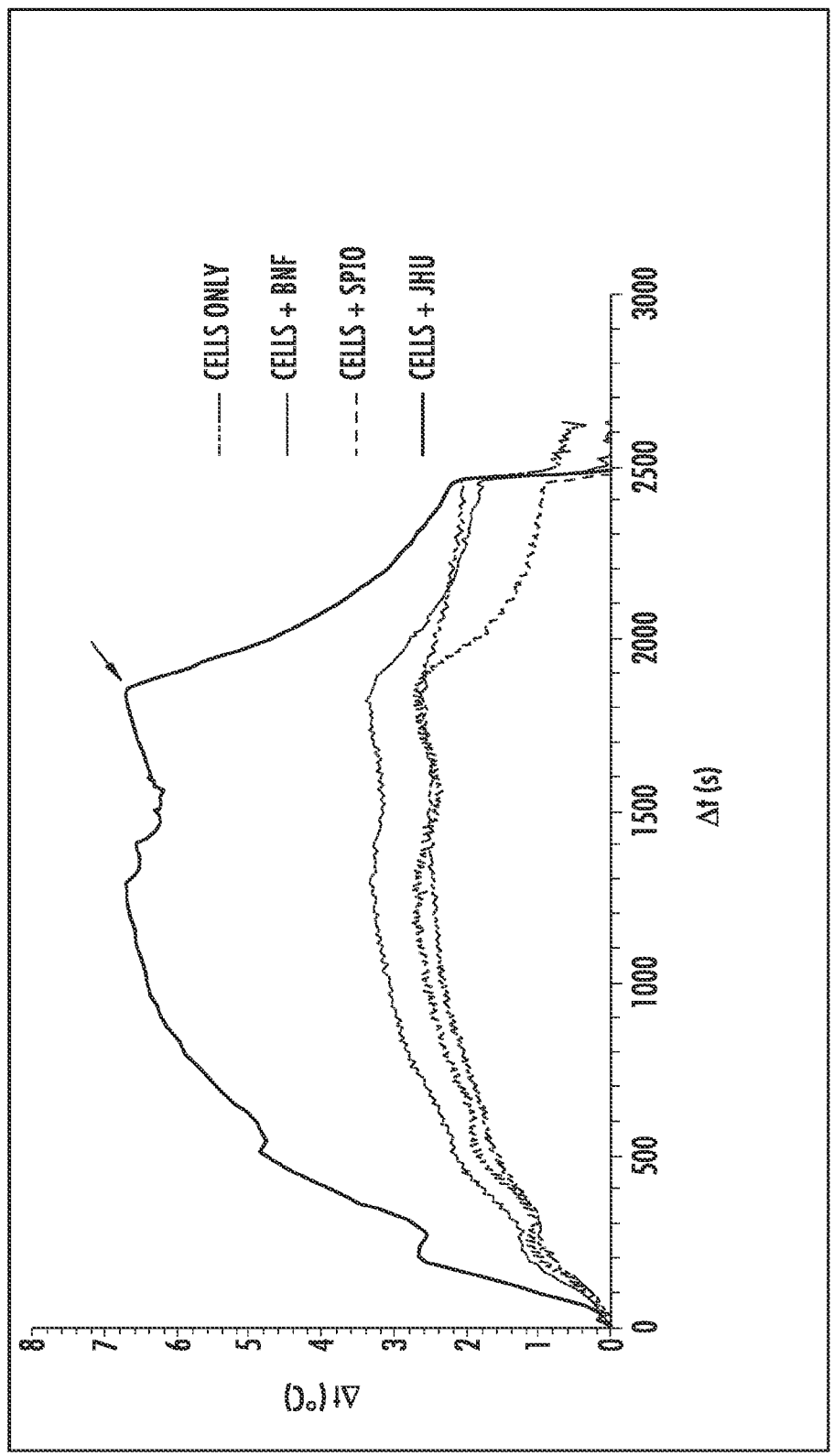
Figure 12:
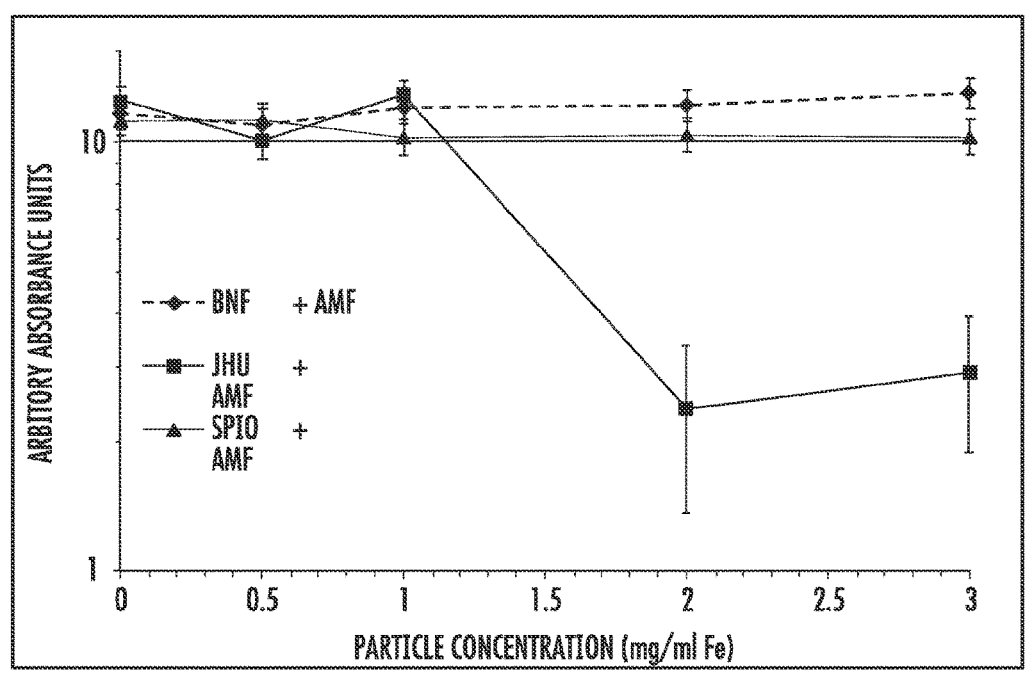
Figure 13:
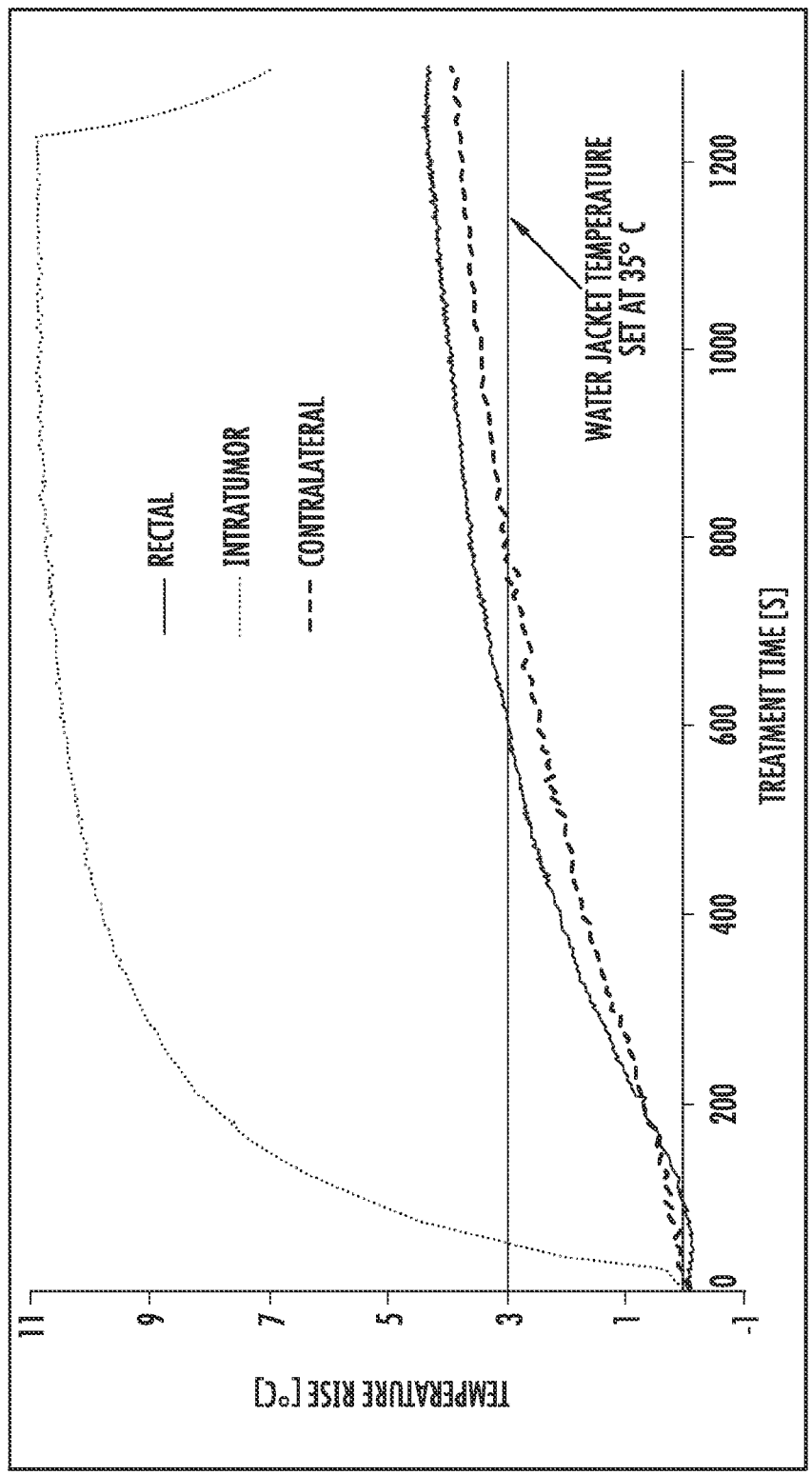
Figure 14:
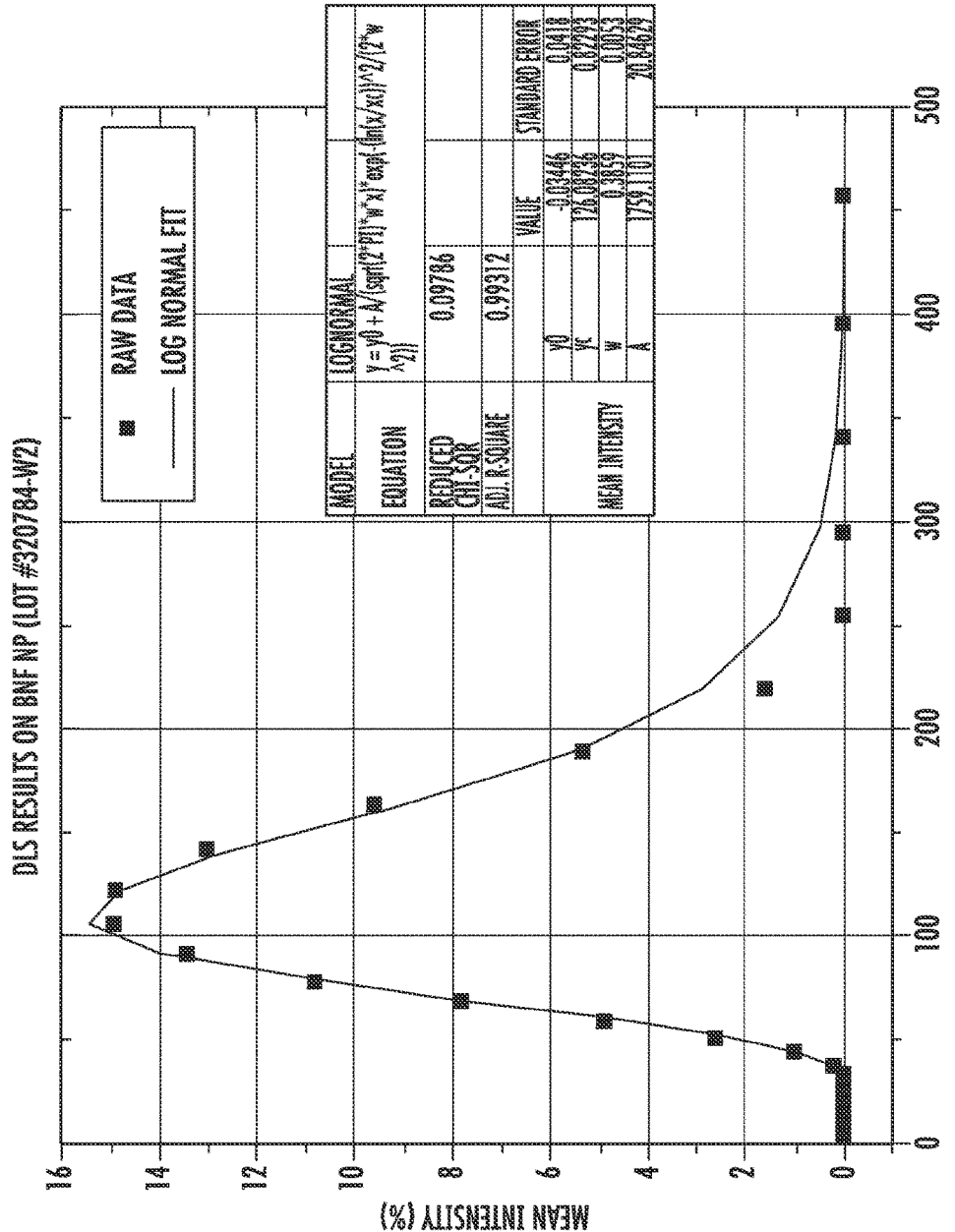
Figure 15:
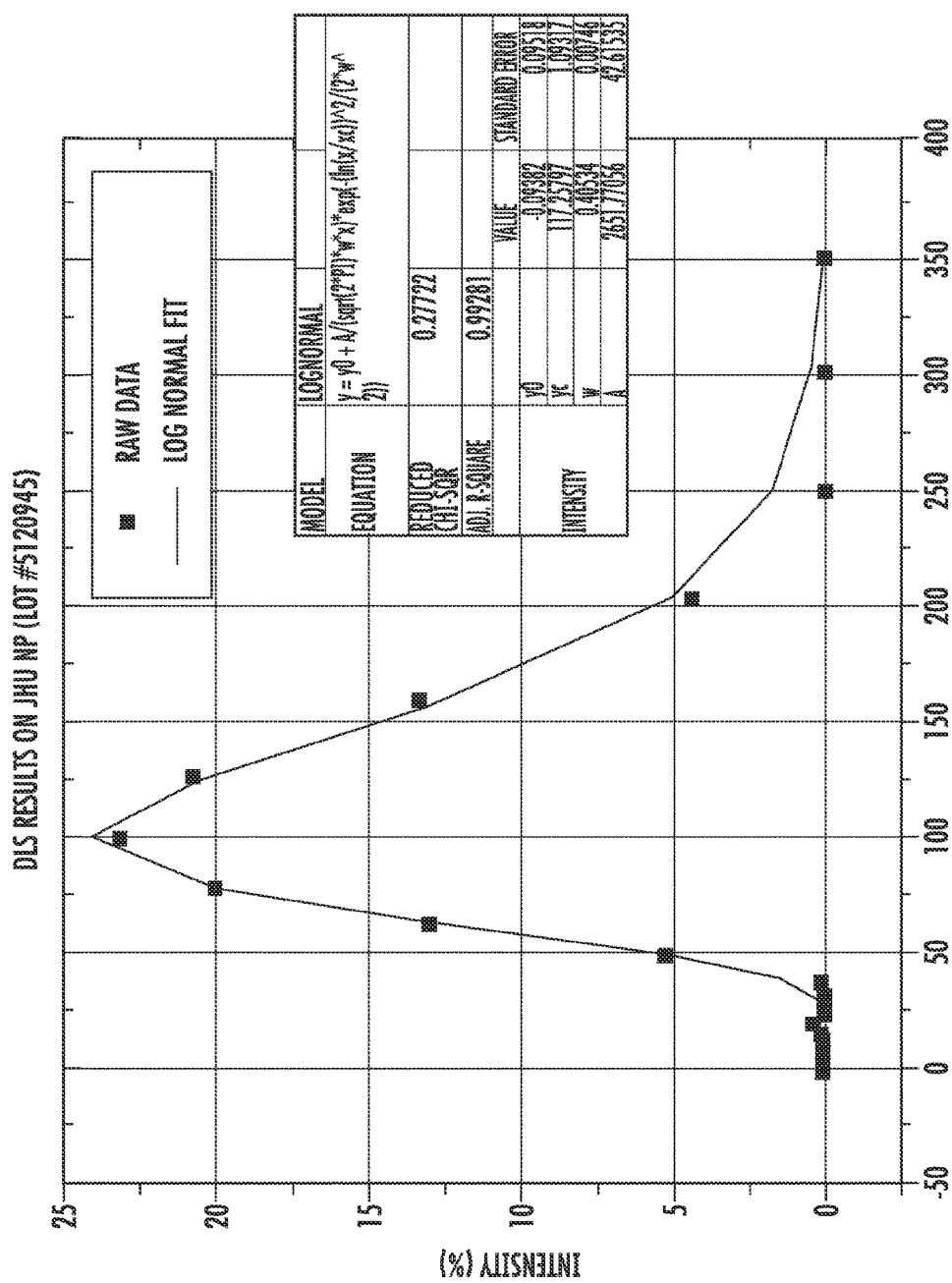
Figure 16:
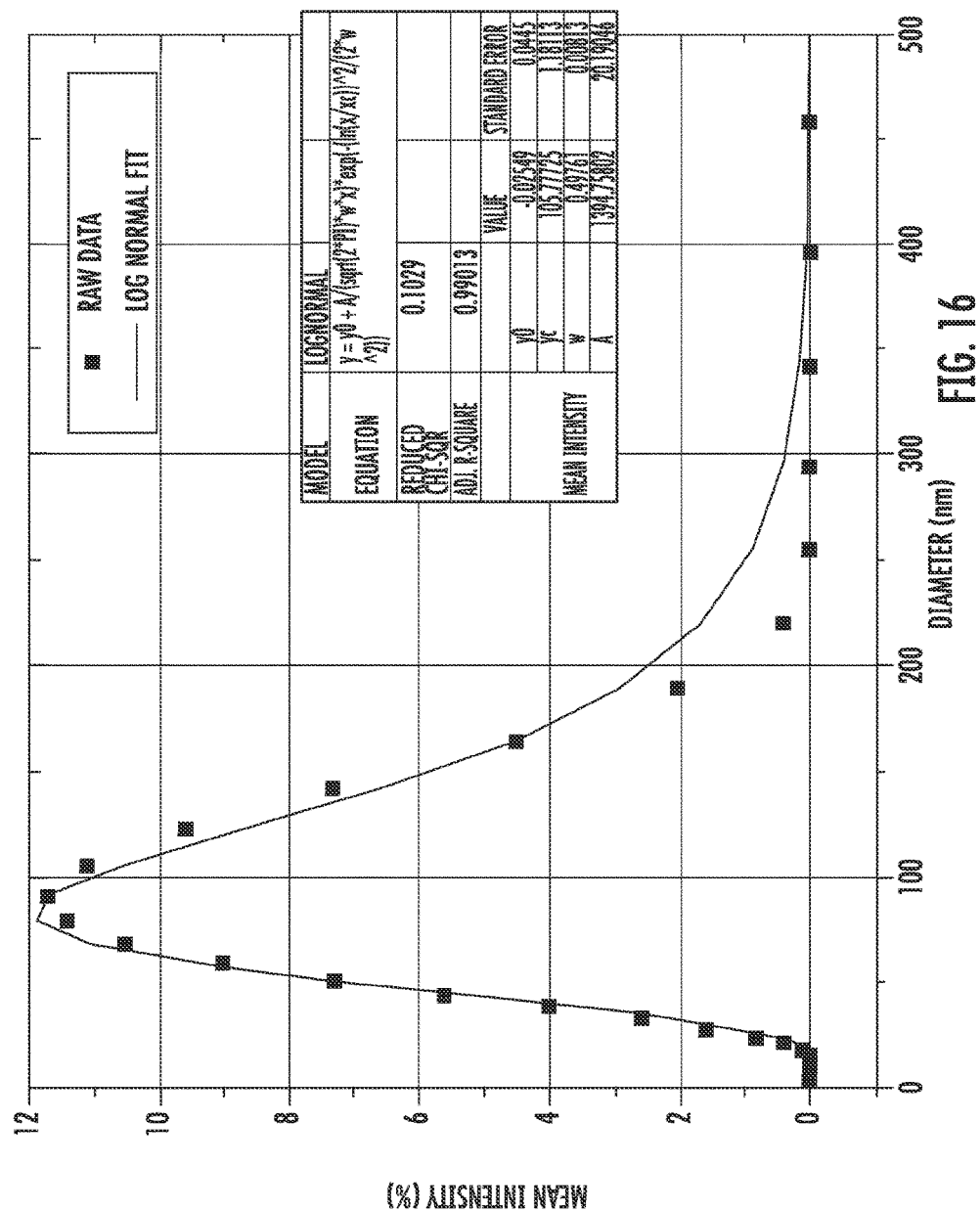
Figure 17:
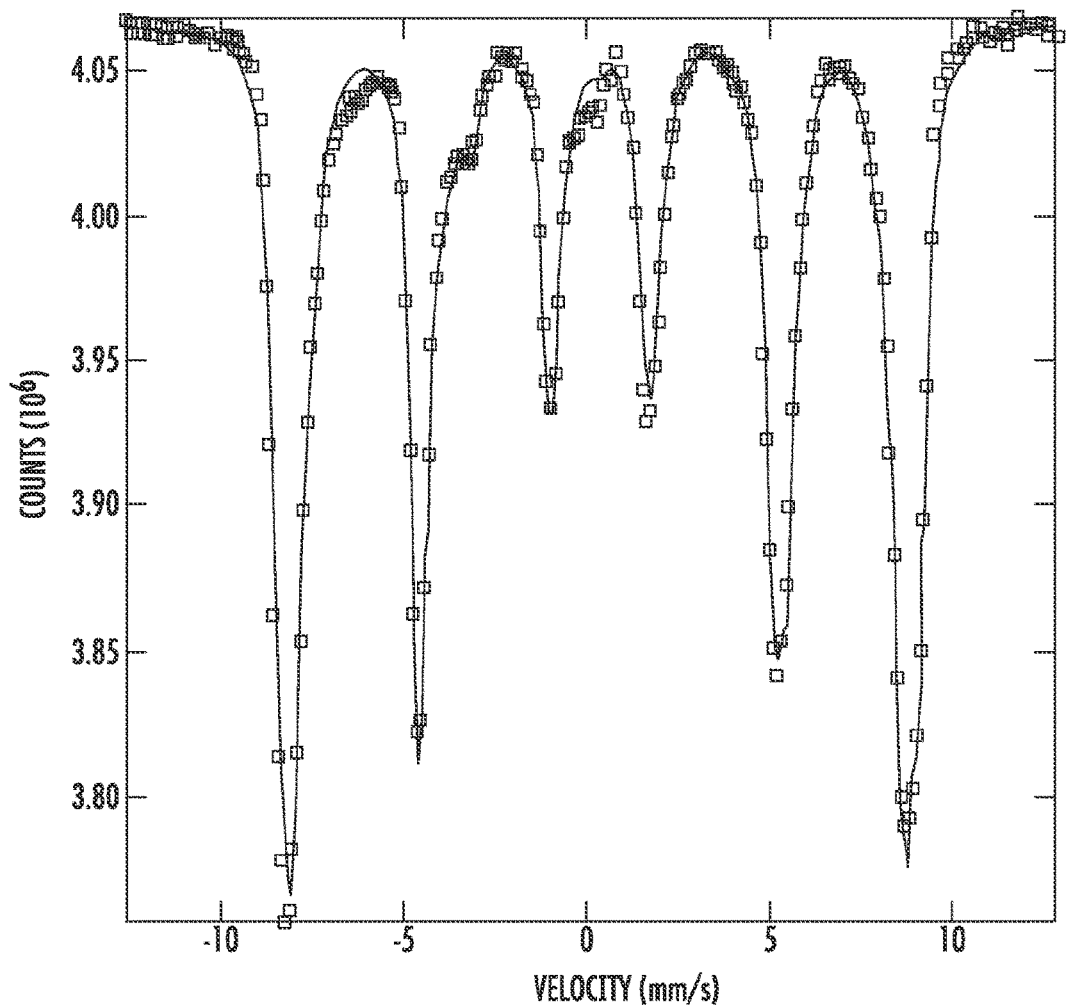
Figure 18:
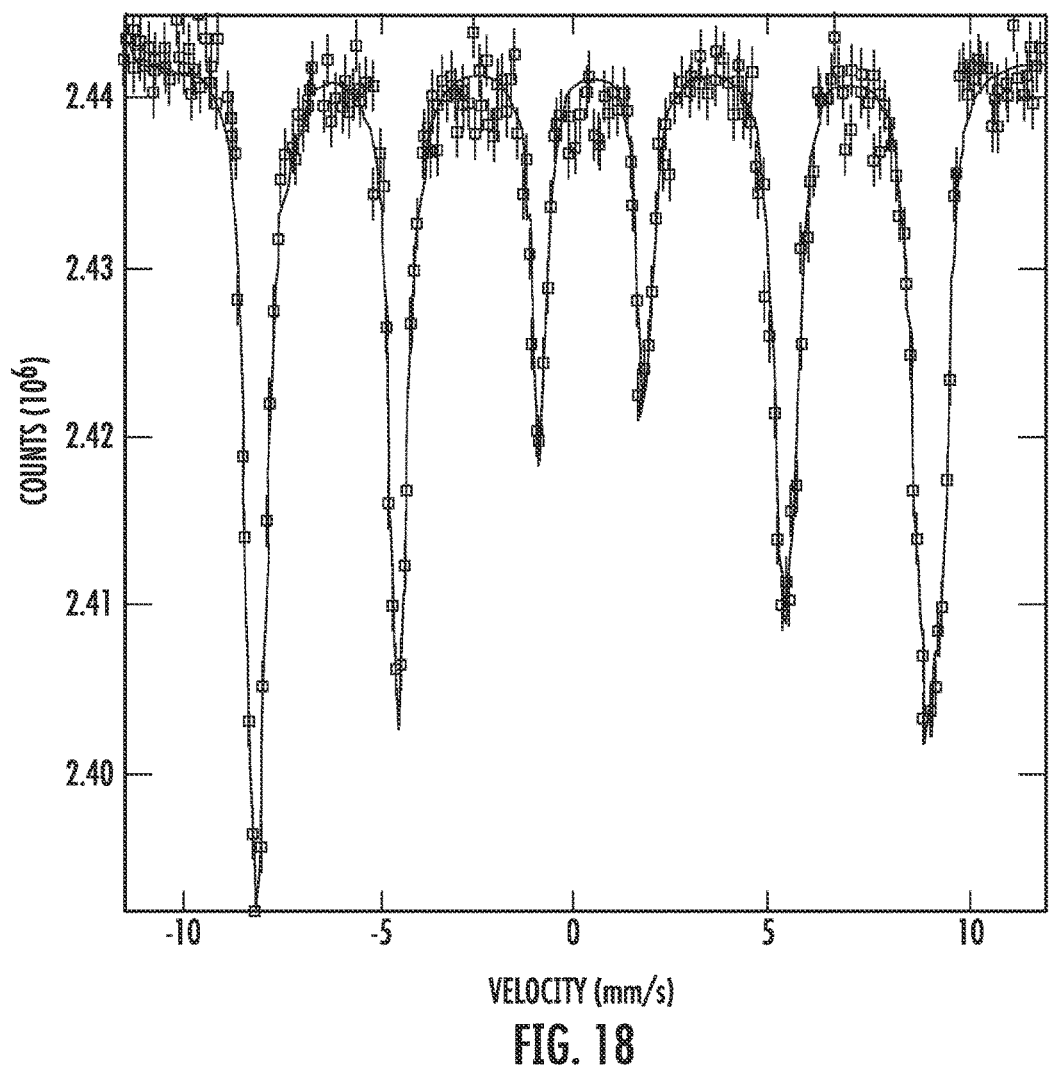
Figure 19:
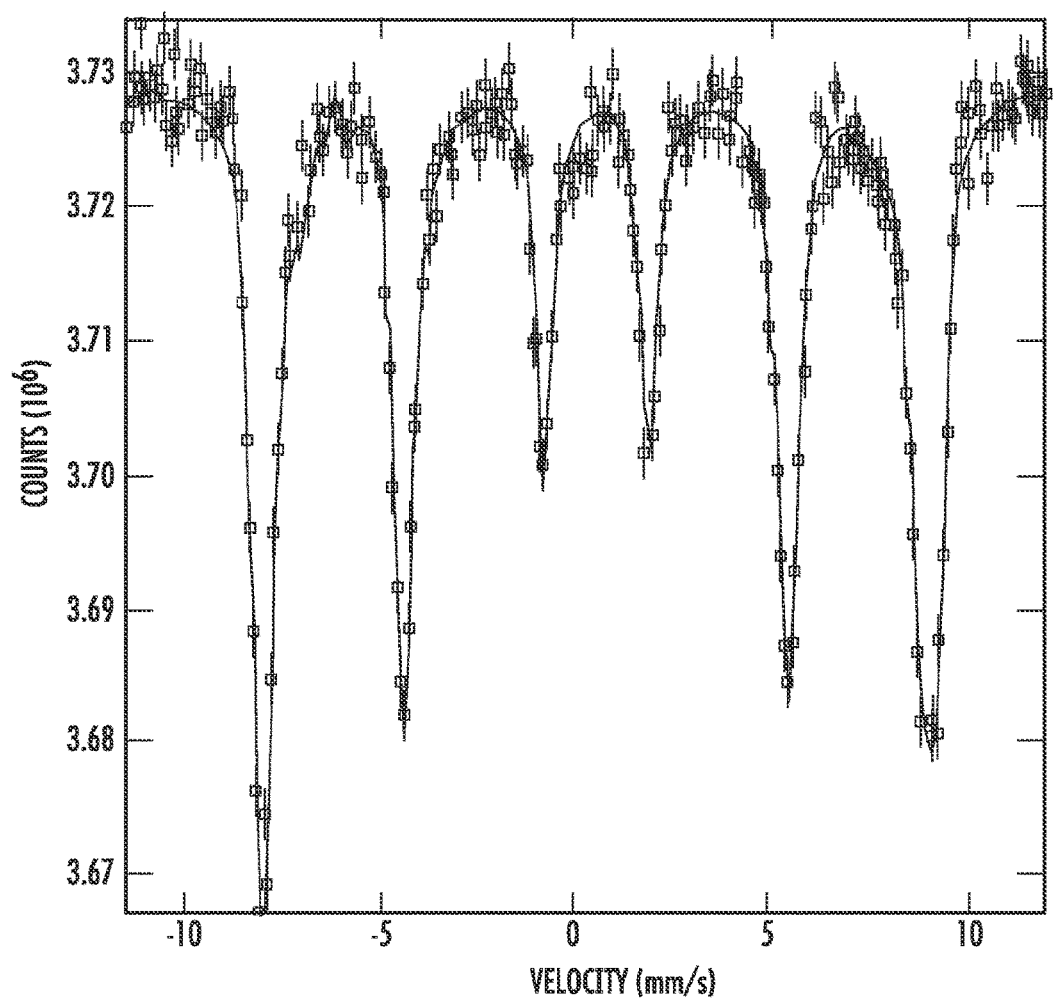
Figure 20A:
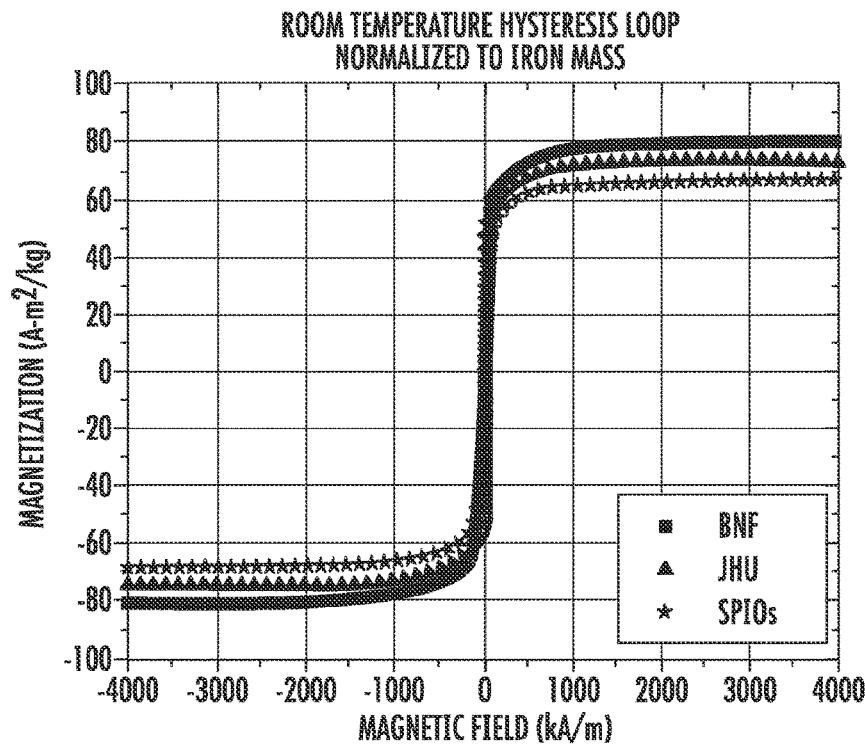
Figure 20B:
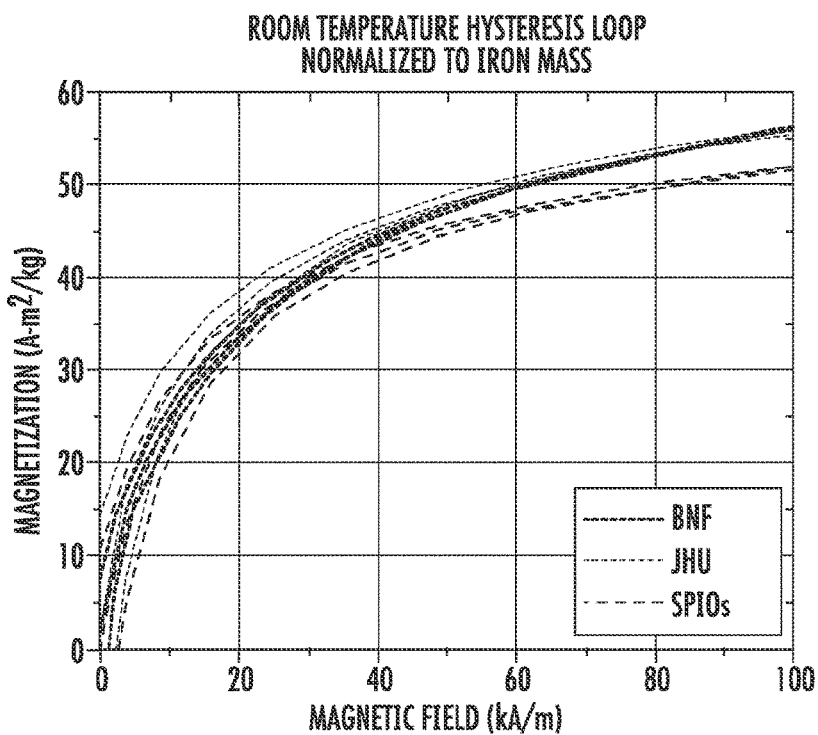
Figure 21:
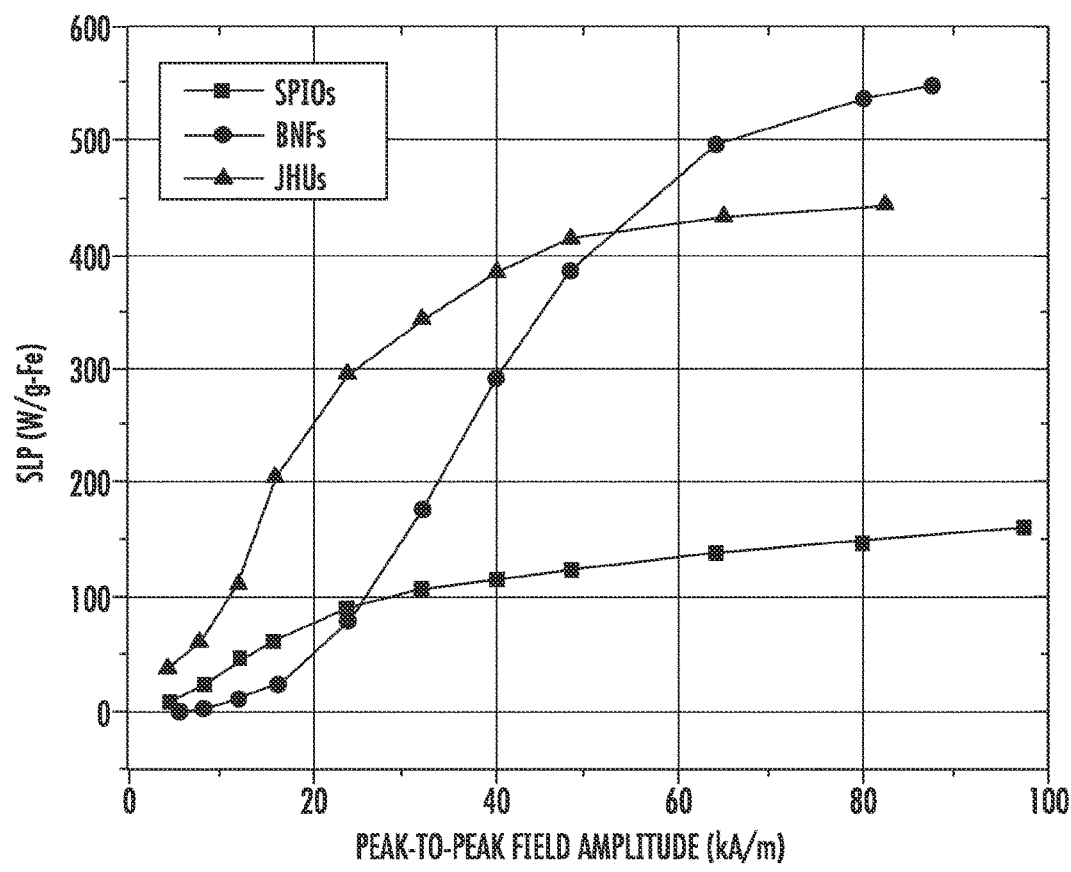
Figure 22:
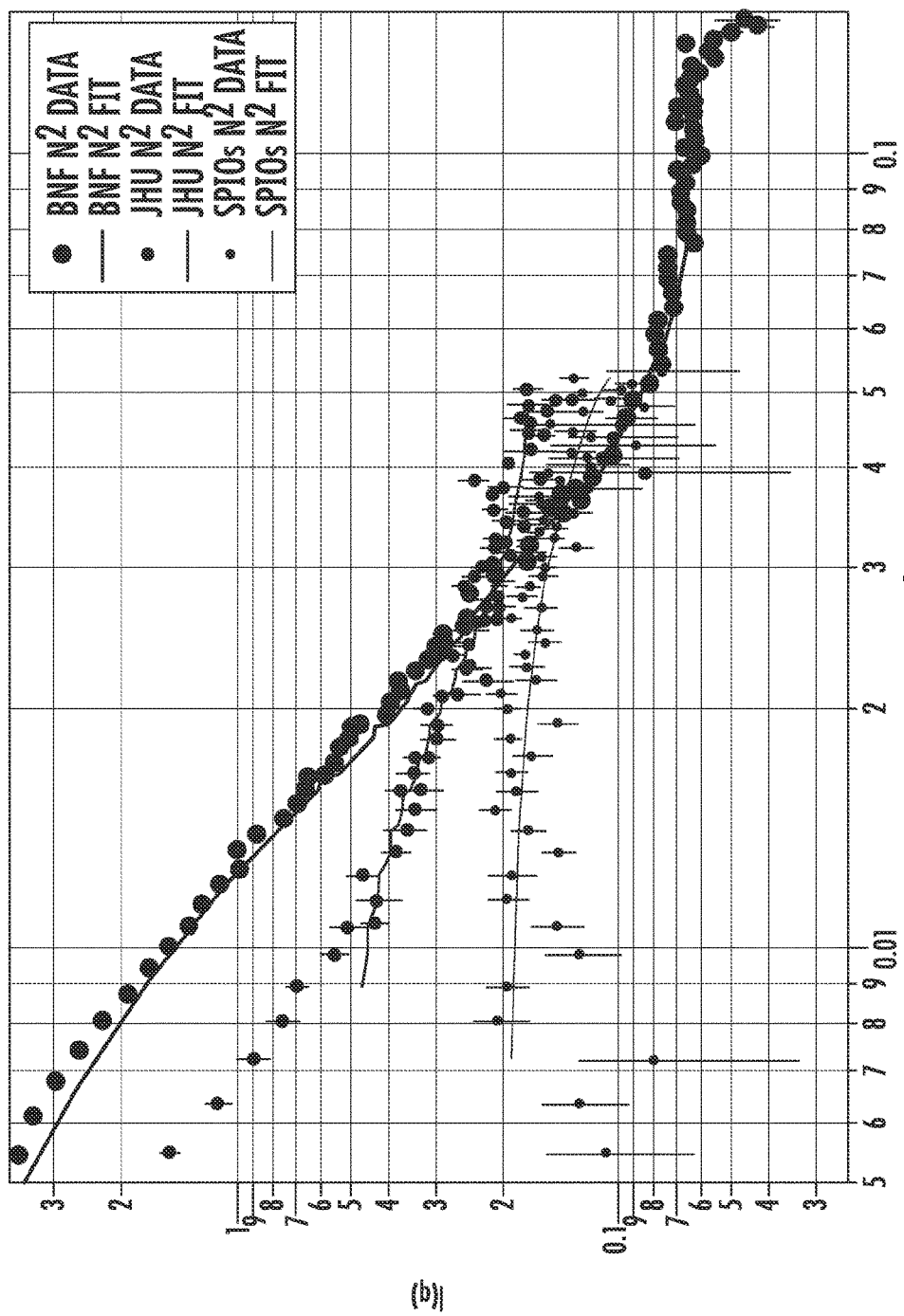
Figure 23:
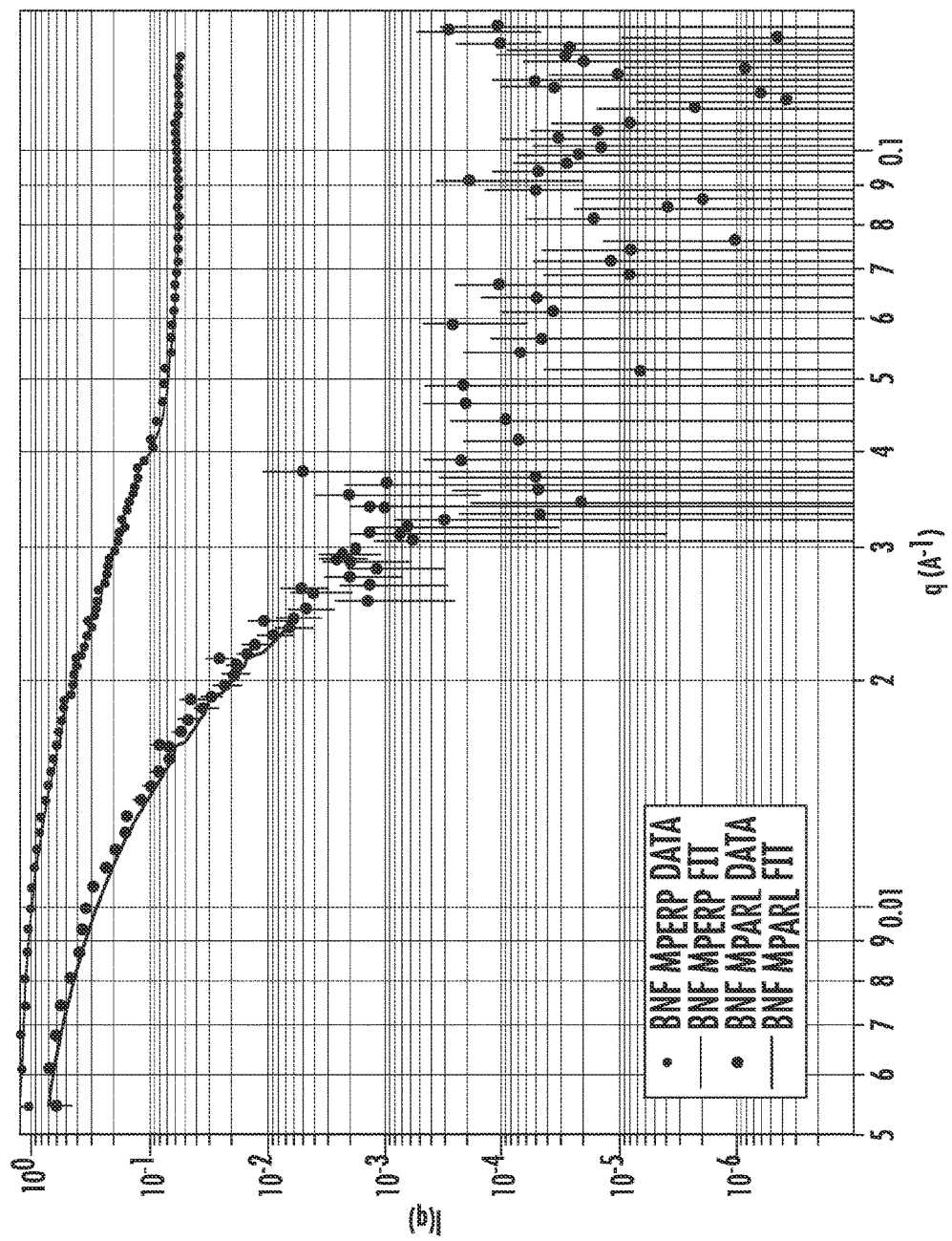
Figure 24:
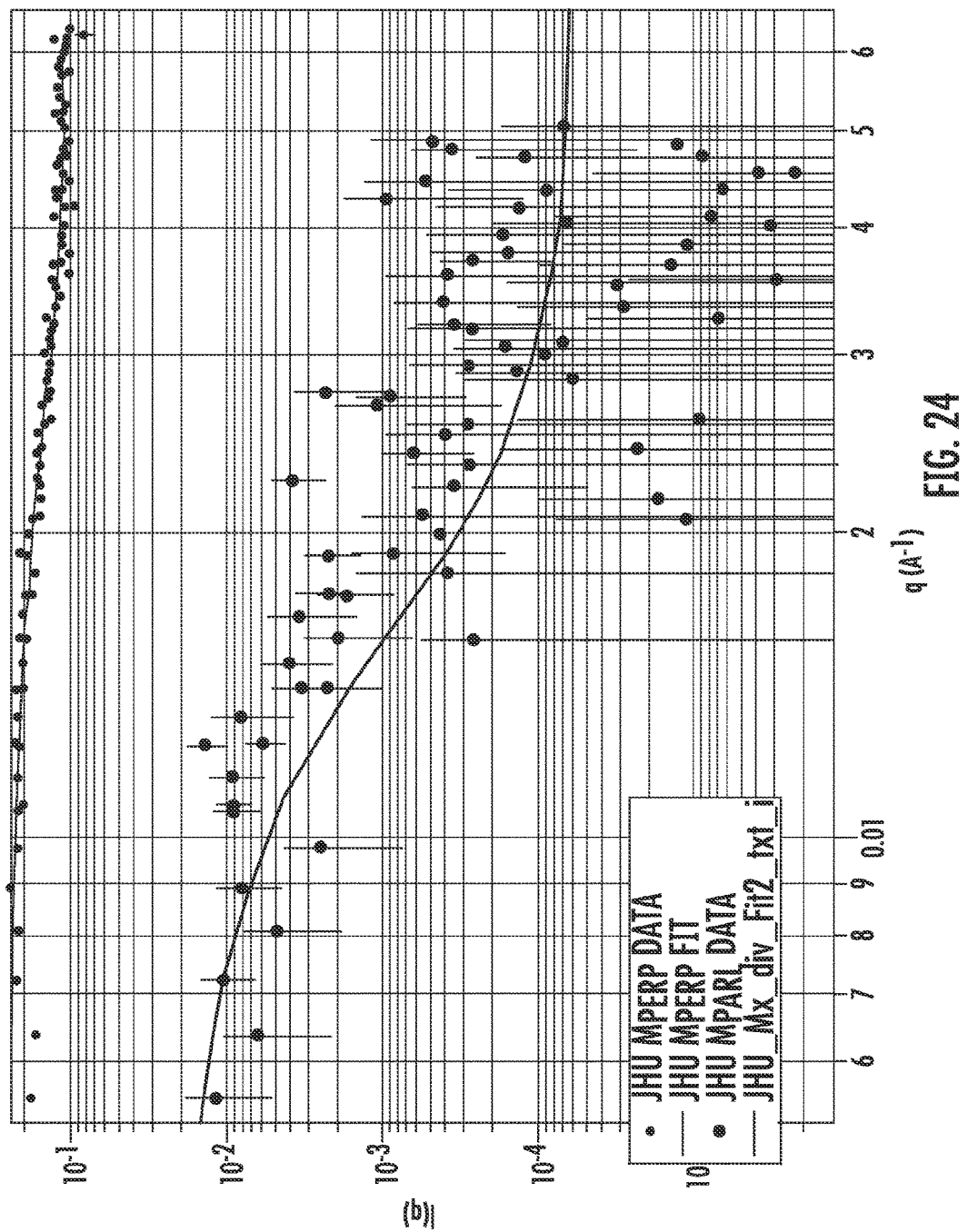
Figure 25:
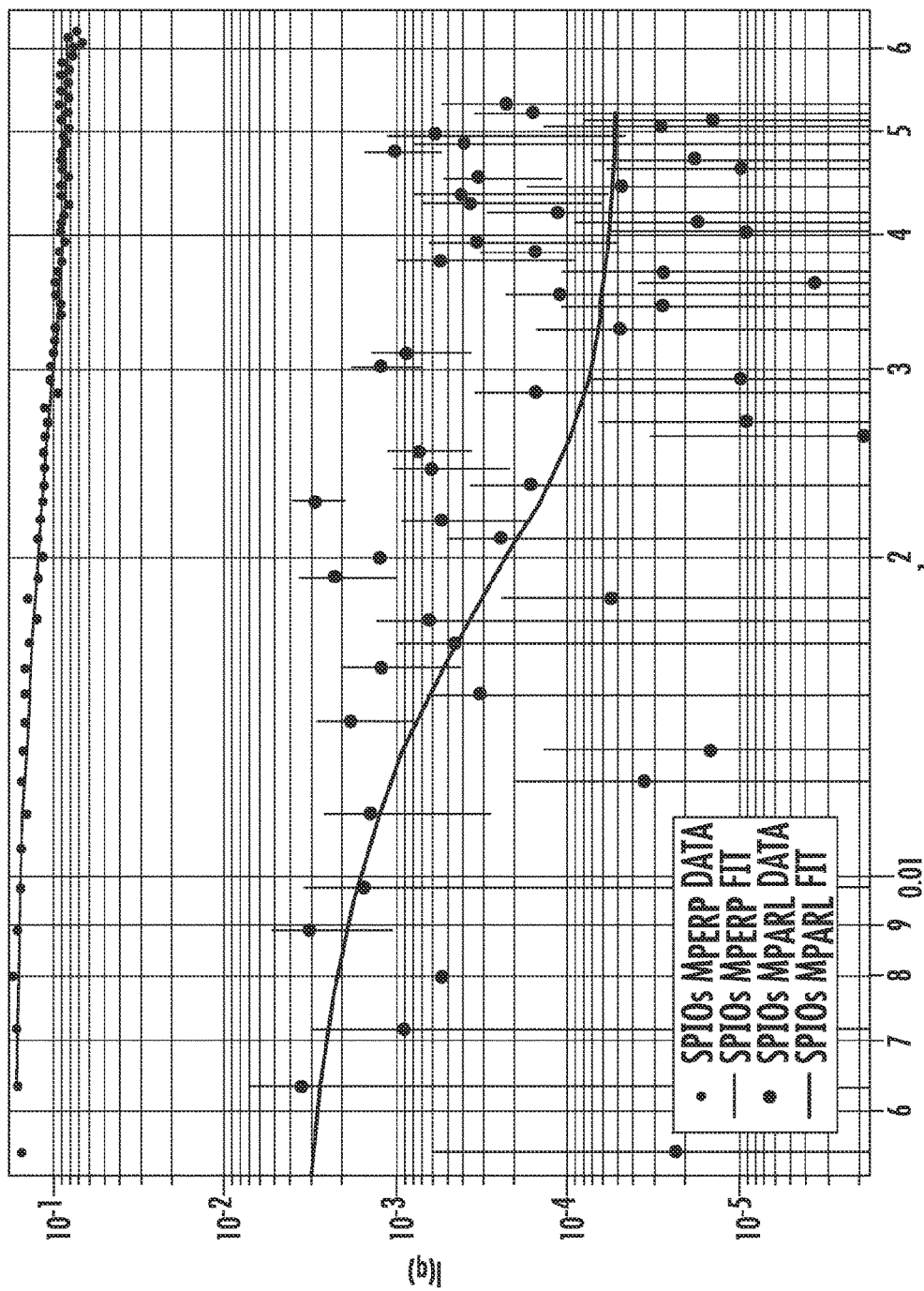

Having thus described the presently disclosed subject matter in general terms, reference will now be made to the accompanying Figures, which are not necessarily drawn to scale, and wherein:

FIGS. 1A-1B show (A) a representative schematic of high gravity controlled precipitation (HGCP) production of particles and (B) X-ray diffraction pattern of the surface modified $Fe_3O_4$ particles;

FIGS. 2A-2C show (A) a scanning electron microscope (SEM) image of a presently disclosed $Fe_3O_4$ particle, (B) a transmission electron microscope (TEM) image of a presently disclosed $Fe_3O_4$ particle, and (C) an electron diffraction pattern of the presently disclosed $Fe_3O_4$ particles;

FIGS. 3A-3C show (A) a representative particle size and size distribution measured by photon-correlation spectroscopy (PCS) of the presently disclosed $Fe_3O_4$ particles, (B) a thermal gravimetric analyzer (TGA) curve of citric acid coated $Fe_3O_4$ particles, and (C) an IR (Infrared) spectrum of citric acid coated $Fe_3O_4$ particles, pure $Fe_3O_4$ particles and pure citric acid;

FIG. 4 shows normalized heating, or specific absorption rate (SAR) plots of citric acid coated $Fe_3O_4$ particles taken for three different samples. One sample was tested (square) immediately post-production, and tested again after three months (diamond);

FIGS. 5A-5C show prostate cancer cell (PC3 and Du145) culture data (A) microscopy of particle uptake in PC3 cells; (B) cytotoxicity of PC3 cells; and, (C) ICP-MS (Inductively Coupled Plasma Mass Spectrometry) data of uptake. Cellular uptake (Du-145) of citrate coated iron oxide NPs in normal and low protein medium;

FIG. 6 shows representative intratumor temperature data;

FIGS. 7A-7C show histology data depicting (A) saline control with AMF (Alternating Magnetic Fields); (B) particle (no AMF) control; and, (C) particle+AMF with necrotic cells inside heat zone near particles and normal outside heat zone;

FIGS. 8A-8B show (A) Rectangular induction coil used to generate AMF for in-vitro experiments; (B) Magnetic field probe used to calibrate/map the AMF amplitude;

FIG. 9 shows cells cultured with in a multi-well plate with 3 different IONPs and a control (cells alone);

FIG. 10 shows a Measured AMF amplitude map along x- and y-axes;

FIG. 11 shows temperature rise profiles of DU145 cells treated with AMF amplitude of 20 kA/m in presence of IONPs at 3 mg of Fe/mL (arrow indicates when the AMF was turned off);

FIG. 12 shows viability of DU145 cells using neutral red assay after AMF treatment at 20 kA/m with different IONPs;

FIG. 13 shows intratumor temperature data in a DU145 xenograft mouse model when exposed to AMF amplitude of 29 kA/m at 155±5 kHz;

FIG. 14 shows Dynamic Light Scattering of the BNF nanoparticles in $H_2O$. The red line is the fit with a Log Normal distribution;

FIG. 15 shows Dynamic Light Scattering of the JHU (Johns Hopkins University) nanoparticles in $H_2O$. The red line is the fit with a LogNormal distribution;

FIG. 16 shows Dynamic Light Scattering of the SPIO nanoparticles in $H_2O$. The red line is the fit with a LogNormal distribution;

FIG. 17 shows the Mossbauer Spectrum of the (dried) BNF nanoparticles at 10K;

FIG. 18 shows the Mossbauer Spectrum of the (dried) JHU nanoparticles at 10K;

FIG. 19 shows the Mossbauer Spectrum of the (dried) SPIO nanoparticles at 10K;

FIGS. 20A-20B show the normalized hysteresis loop of the BNF, JHU, and SPIO nanoparticles in $H_2O$ at 300K. (A) full hysteresis loop and (B) portion of hysteresis loop in fields achievable in this hyperthermia experiment. The moment is normalized to the iron concentration. Sample holder and water contributions are removed, but contributions from the dextran remain;

FIG. 21 shows the Specific Loss Power (SLP) of the BNF (red circles), JHU (green triangles), and SPIO (black squares) nanoparticles in $H_2O$ at 150 kHz as a function of peak-to-peak magnetic field amplitude. The moment is normalized to the iron concentration;

FIG. 22 shows the nuclear scattering only contribution to the polarized beam SANS data of the BNF, JHU, and SPIO nanoparticles in $D_2O$ at room temperature;

FIG. 23 shows the magnetic scattering contributions (parallel and perpendicular to the field) to the polarized beam SANS data of the BNF nanoparticles in $D_2O$ at room temperature;

FIG. 24 shows the magnetic scattering contributions (parallel and perpendicular to the field) to the polarized beam SANS data of the JHU nanoparticles in $D_2O$ at room temperature; and FIG. 25 shows the magnetic scattering contributions (parallel and perpendicular to the field) to the polarized beam SANS data of the SPIO nanoparticles in $D_2O$ at room temperature.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Magnetic nanoparticle hyperthermia (mNHP) is regarded as a promising minimally invasive procedure. These nanoparticles generate heat when exposed to alternating magnetic fields (AMFs) and thus have shown a potential for selective delivery of heat to a target such as a cancer cell. Despite the great promise however, successful clinical translation has been limited in part by technical challenges of selectively delivering heat only to the target tissue. Interaction of AMF with tissues also deposits heat through Joule heating via eddy currents. Considerations of patient safety thus constrain the choice of AMF power and frequency to values that are insufficient to produce desirable heating from available nanoparticle formulations. Therefore, considerable effort must be directed to the design of particles and the AMF device to maximize the specific delivery of heat to the intended target while minimizing the unintended and non-specific heating.

The presently disclosed subject matter provides iron-oxide nanoparticles (IONPs) having much higher heating capability at the clinically relevant amplitudes and frequencies than other formulations. As disclosed herein, a rectangular coil designed for treating multi well tissue culture plate is utilized and it is shown that the presently disclosed particles are superior to two commercially available IONPs for hyperthermia of DU145 prostate cancer cells in culture. Results of pilot in-vivo experiments using the DU145 human prostate xenograft model in nude male mouse are reported. AMF treatment yielded an intratumor temperature rise >10° C. in <10 min heating (AMF amplitude 29 kA/m @160 kHz) with approximately 4 mg nanoparticle/g tumor while maintaining rectal (core) temperature well within physiological range.

I. METHODS FOR MAKING IRON OXIDE NANOPARTICLE PREPARATIONS

In some embodiments, the presently disclosed subject matter provides methods using high gravity controlled precipitation (HGCP) technology for making the presently disclosed iron oxide nanoparticles.

In some embodiments, the presently disclosed subject matter provides a process for preparing one or more surfactant-coated magnetic metal oxide particles, the process comprising: (a) providing a salt solution of a metal; (b) contacting the salt solution of the metal with a precipitant solution to form a reactant solution; (c) rapidly micro-mixing the reactant solution to initiate formation of metal oxide crystals under controlled nucleation conditions; (d) continuing to rapidly micro-mix the reactant solution under high gravity conditions to control crystal growth of one or more metal oxide particles formed therein; (e) coating the one or more metal oxide particles with a surfactant; (f) separating the one or more coated metal oxide particles from the reactant solution and one or more by-products, if present, formed therein; and (g) exposing the one or more coated metal oxide particles to high temperature and high pressure in an inert gas environment for a period of time to form one or more surfactant-coated magnetic metal oxide particles.

In some embodiments, the reactant solution comprises an iron precursor solution comprising anhydrous $FeCl_3$ and $FeCl_2 \cdot 4H_2O$ in hydrochloric acid. In some embodiments, the salt solution comprises a metal salt comprising a metal selected from the group consisting of Fe, Co, Ni, and Sm. In further embodiments, the metal salt comprises an anionic species selected from the group consisting of chloride, bromide, fluoride, iodide, nitrate ($NO_3$), sulfate ($SO_4$), chlorate ($ClO_4$), and phosphate ($PO_4$).

In some embodiments, the precipitant solution comprises ammonia. In other embodiments, the precipitant solution comprises at least one member selected from the group consisting of NaOH, ammonium hydroxide ($NH_4OH$), and another hydroxide of Group I or II elements from the Periodic Table of elements. In further embodiments, the reactant solution comprises at least one member selected from the group consisting of a hydroxide, a carbonate, and a phosphate.

In some embodiments, the coating comprises citric acid. In other embodiments, the surfactant is selected from the group consisting of an organic acid, a lipid, a phospholipid, an oleate, an ester, a sulfate, a diol, and a polymer.

In particular embodiments, the exposing of the one or more coated metal oxide particles to high temperature and high pressure is conducted at about 130° C. for about 5 hours.

In further embodiments, as described in more detail herein below, the presently disclose subject matter provides one or more surfactant-coated magnetic metal oxide particles prepared by the presently disclosed methods.

One characteristic of the nano- or micro-particles produced by these methods is that they need to provide uniform heating at many sites. Such uniform heating requires a predictable or uniform dose and dosimetry. The alternating magnetic field (AMF) amplitude must be uniformly applied to a large volume of tissue. The appreciable tissue volume exposure limits field amplitude to about 15-24 kA/m. Therefore, the presently disclosed particles are capable of producing substantial heating at low amplitude fields. To provide these characteristics, the presently disclosed subject matter provides high-gravity controlled precipitation methods to prepare the base iron oxide crystal. The iron oxide crystals are coated with a weak, organic acid, such as citric acid, to ensure charge stabilization, resulting in colloid stability.

Nano- or micro-particles can be obtained by rapid micro-mixing of reactants to enhance nucleation while suppressing crystal growth. Thorough micro-mixing leads to uniform crystal growth and therefore uniform particle size can be obtained. On the other hand, insufficient micro-mixing will lead to growth disparity among different nuclei, resulting in a wide particle size distribution (PSD). There are two characteristic time parameters in crystallization: the induction time (T) and the micro-mixing time ($t_m$). When $t_m \ll T$, the nucleation rate will be nearly uniform spatially, and the PSD can be controlled at a uniform level. This can be achieved by a High Gravity Controlled Precipitation (HGCP) reactor which utilizes a rotating packed bed to intensify mass and heat transfer in multiphase systems. During rotation, the fluids going through the packed bed are spread and split into thin films, threads and very fine droplets under the high shear force created by the high gravity. This results in intense micro-mixing between the fluid elements by one to three orders of magnitude. The micro-mixing time ($t_m$) in this process is estimated to be around the magnitude of the order of 10-100 µs in the presently disclosed methods.

II. IRON OXIDE NANOPARTICLE COMPOSITIONS

As used herein, the terms "nanoparticle" refers to one or more structures that have at least one dimension, e.g., a height, width, length, and/or depth, in a range from about one nanometer (nm), i.e., $1 \times 10^{-9}$ meters, to about 999 nm, including any integer value, and fractional values thereof, including about 1, 2, 5, 10, 20, 30, 40, 50, 60, 70, 80, 90, 100, 200, 500, 600, 700, 800, 900, 999 nm and the like.

In some embodiments, the presently disclosed subject matter provides a magnetic metal oxide nanoparticle prepared from a high-gravity controlled precipitation reaction, the nanoparticle comprising: (a) iron oxide crystals having a dimension ranging from about 5 nm to about 100 nm; and (b) a surfactant coating; wherein the nanoparticle has a heating property of greater than about 60 W/g Fe in an alternating current (AC) magnetic field having a frequency of ranging from about 50 kHz and to about 1 MHz and an amplitude ranging from about 0.080 kA/m to about 50 kA/m.

Generally, the one or more surfactant-coated magnetic metal oxide particles have a substantially isotropic shape and have a dimension ranging from about 50 nm to about 100 nm. More particularly, the particles comprise about 76% $Fe_3O_4$ and about 24% $\gamma$-$Fe_2O_3$ and are substantially free of $Fe(OH)_2$.

In further embodiments, the presently disclosed subject matter provides a magnetic nanoparticle comprising: (a) a magnetic core comprising an aggregate of at least two magnetic crystalline grains, wherein the aggregate exhibits a collective magnetic phase such that the core has an apparently single magnetic domain phase; (b) a second magnetic phase or magnetic oxide phase differing from the collective or single domain phase of the core, wherein the second magnetic phase or magnetic oxide phase can intercalate and surround the core; wherein at least one magnetic phase exhibits a "hard" or high-coercive behavior in a magnetic field and at least one other phase exhibits a "soft" or low-coercive behavior in a magnetic field relative to the "hard" magnetic phase; and (c) a coating. More particularly, the core substantially comprises $Fe_3O_4$ and the second magnetic phase or magnetic oxide phase substantially comprises $\gamma$-$Fe_2O_3$.

In some embodiments, the nanoparticles may comprise a coating. The coating may enhance the heating properties of the nanoparticles and/or may comprise radioactive or potentially radioactive elements. Suitable materials for the coating include synthetic and biological polymers, copolymers and polymer blends, and inorganic materials. Polymer materials may include various combinations of polymers of acrylates, siloxanes, styrenes, acetates, akylene glycols, alkylenes, alkylene oxides, parylenes, lactic acid, and glycolic acid. Further suitable coating materials include a hydrogel polymer, a histidine-containing polymer, and a combination of a hydrogel polymer and a histidine-containing polymer.

Coating materials may also include combinations of biological materials, such as a polysaccharide, a polyaminoacid, a protein, a lipid, a glycerol, and a fatty acid. Examples of other biological materials suitable for use herein include heparin, heparin sulfate, chondroitin sulfate, chitin, chitosan, cellulose, dextran, alginate, starch, carbohydrate, and glycosaminoglycan. Examples of proteins useful herein include an extracellular matrix protein, proteoglycan, glycoprotein, albumin, peptide, and gelatin. These materials may also be used in combination with any suitable synthetic polymer material.

Inorganic coating materials may include any combination of a metal, a metal alloy, and a ceramic. Examples of ceramic materials suitable for use herein include a hydroxyapatite, silicon carbide, carboxylate, sulfonate, phosphate, ferrite, phosphonate, and oxides of Group IV elements of the Periodic Table of Elements. These materials may form a composite coating that may also contain one or more biological or synthetic polymers. Where the magnetic particle is formed from a magnetic material that is biocompatible, the surface of the particle itself operates as the biocompatible coating.

The coating material may also serve to facilitate transport of the nanoparticles into a cell, a process known as transfection. Such coating materials, referred to as transfection agents, include vectors, prions, polyaminoacids, cationic liposomes, amphiphiles, and non-liposomal lipids or any combination thereof. A suitable vector may be a plasmid, a virus, a phage, a viron, a viral coat. The nanoprobe coating may be a composite of any combination of transfection agent with organic and inorganic materials, such that the particular combination may be tailored for a particular type of a diseased material and a specific location within a patient's body.

In further embodiments, the presently disclosed subject matter provides a biocompatible suspension comprising a presently disclosed magnetic metal oxide nanoparticle and water.

In still further embodiments, the presently disclosed subject matter provides a kit for preventing and/or treating a cell disorder or diseased tissue by using at least one magnetic metal oxide particle of the presently disclosed subject matter. In an embodiment, the presently disclosed subject matter provides a kit for treating a diseased tissue, the kit comprising a magnetic metal oxide nanoparticle prepared from a high-gravity controlled precipitation reaction.

III. METHODS FOR USING IRON OXIDE NANOPARTICLES

Metastatic cancer is characterized by diffuse disease with occult and widespread metastatic lesions, and is typically refractory to standard of care therapies. Heat is a potent sensitizer of cancer to both radiation and some chemotherapeutic agents. Delivering the heat selectively to cancer tumors, however, particularly those typical of metastatic disease represents a challenge that has not yet been adequately addressed. Magnetic nanoparticles that are capable of localizing to these sites and heating when exposed to an AC magnetic field allow depositing of heat to these tumor sites with little adverse damage to surrounding normal tissue. To be effective, the nanoparticles must be capable of generating substantial heat (>100 W/g Fe) when exposed to low frequency (100 kHz to 300 kHz) and low power (peak-to-peak amplitude 10 kA/m to 30 kA/m) AC fields. These latter constraints are necessary to avoid overheating the patient by nonspecific heating that results from interactions of large volumes of tissue with the electromagnetic field.

Generally, in some embodiments, the presently disclosed subject matter provides a method for treating a diseased tissue, the method comprising: (a) administering to a tissue or a subject in need of treatment thereof, a therapeutically effective amount of a magnetic nanoparticle comprising surfactant-coated iron oxide crystals prepared from a high-gravity controlled precipitation process; and (b) subjecting the tissue or subject, or a portion of the tissue or subject to an alternating current (AC) magnetic field having frequency ranging from about 50 kHz to about 1 MHz and having an amplitude (peak-to-peak) ranging from about 0.080 kA/m to about 50 kA/m.

In one embodiment, the presently disclosed nanoparticles are used as therapeutic drugs for cell disorders. In some embodiments, the cell disorder may be, but is not limited to, cancer. In other embodiments, the presently disclosed nanoparticles may be used in other diseases, where eliminating aberrant cells or modulating an aberrant cellular function would be useful. Aberrant cells include, but are not limited to, cells infected by a virus and cells infected by a bacterium. Therefore, the cell disorder may be associated with diseases, such as cancer, diseases of the immune system, pathogen-borne diseases, and undesirable targets, such as toxins, reactions to organ transplants, hormone-related diseases, and non-cancerous diseased cells or tissue.

In some embodiments, the presently disclosed subject matter has use in treating a cell disorder, such as cancer, and thus provides a method of treating a cell disorder. More specifically, in some embodiments, the method has use in treating or preventing a cell disorder in a subject.

The methods of the invention generally comprise contacting at least one cell with at least one nanoparticle. The methods thus can be practiced in vitro, in vivo, and ex vivo. They accordingly may be practiced, for example, as a research method to identify compounds or to determine the effects of compounds and concentrations of compounds, as a therapeutic method of treating a cell disorder, and as a method to prevent a cell disorder. In embodiments where the method is a method of treating, it can be a method of therapy (e.g., a therapeutic method) in which the amount administered is an amount that is effective for reducing or eliminating a cell disorder. In embodiments where the method is a method of prevention, the amount is an amount sufficient to prevent the cell disorder from occurring or sufficient to reduce the severity of the cell disorder if it does occur.

A presently disclosed nanoparticle can be targeted to a cell with a disorder by using ligands on the nanoparticle. The ligand may be a polyclonal antibody, a monoclonal antibody, a chimeric antibody, a humanized antibody, a human antibody, a recombinant antibody, a bispecific antibody, an antibody fragment, a recombinant single chain antibody fragment, or any combination of the above.

The choice of a marker (antigen) may be important in the targeted therapy methods of the presently disclosed subject matter. Although not limited thereto, use and selection of markers is most prevalent in cancer immunotherapy. For breast cancer and its metastases, a specific marker or markers may be selected from cell surface markers such as, for example, members of the MUC-type mucin family, an epithelial growth factor (EGFR) receptor, a carcinoembryonic antigen (CEA), a human carcinoma antigen, a vascular endothelial growth factor (VEGF) antigen, a melanoma antigen (MAGE) gene, family antigen, a T/Tn antigen, a hormone receptor, growth factor receptors, a cluster designation/differentiation (CD) antigen, a tumor suppressor gene, a cell cycle regulator, an oncogene, an oncogene receptor, a proliferation marker, an adhesion molecule, a proteinase involved in degradation of extracellular matrix, a malignant transformation related factor, an apoptosis related factor, a human carcinoma antigen, glycoprotein antigens, DF3, 4F2, MGFM antigens, breast tumor antigen CA 15-3, calponin, cathepsin, CD 31 antigen, proliferating cell nuclear antigen 10 (PC 10), and pS2.

For other forms of cancer and their metastases, a specific marker or markers may be selected from cell surface markers such as, for example, a member of vascular endothelial growth factor receptor (VEGFR) family, a member of carcinoembryonic antigen (CEA) family, a type of anti-idiotypic mAB, a type of ganglioside mimic, a member of cluster designation/differentiation antigens, a member of epidermal growth factor receptor (EGFR) family, a type of a cellular adhesion molecule, a member of MUC-type mucin family, a type of cancer antigen (CA), a type of a matrix metalloproteinase, a type of glycoprotein antigen, a type of melanoma associated antigen (MAA), a proteolytic enzyme, a calmodulin, a member of tumor necrosis factor (TNF) receptor family, a type of angiogenesis marker, a melanoma antigen recognized by T cells (MART) antigen, a member of melanoma antigen encoding gene (MAGE) family, a prostate membrane specific antigen (PMSA), a small cell lung carcinoma antigen (SCLCA), a T/Tn antigen, a hormone receptor, a tumor suppressor gene antigen, a cell cycle regulator antigen, an oncogene antigen, an oncogene receptor antigen, a proliferation marker, a proteinase involved in degradation of extracellular matrix, a malignant transformation related factor, an apoptosis-related factor, a type of human carcinoma antigen.

For ovarian cancers and their metastases, a specific marker or markers may be selected from cell surface markers such as, for example, one of ERBB2 (HER-2) antigen and CD64 antigen. For ovarian and/or gastric cancers and their metastases, a specific marker or markers may be selected from cell surface markers such as, for example, a polymorphic epithelial mucin (PEM). For ovarian cancers and their metastases, a specific marker or markers may be selected from cell surface markers such as, for example, one of cancer antigen 125 (CA125) or matrix metalloproteinase 2 (MMP-2). For gastric cancers and their metastases, a specific marker or markers may be selected from cell surface markers such as, for example, one of CA 19-9 antigen and CA242 antigen.

For non-small cell lung cancer (NSCLC), colorectal cancer (CRC) and their metastases, a specific marker or markers may be selected from cell surface markers such as, for example, vascular endothelial growth factor receptor (VEGFR), anti-idiotypic mAb, and carcinoembryonic antigen (CEA) mimic. For at least one of small-cell lung cancer (SCLC), malignant melanoma, and their metastases, a specific marker or markers may be selected from cell surface markers such as, for example, anti-idiotypic mAB or GD3 ganglioside mimic. For melanoma cancers and their metastases, a specific marker or markers may be selected from cell surface markers such as, for example, a melanoma associated antigen (MAA). For small cell lung cancers and their metastases, a specific marker or markers may be selected from cell surface markers such as, for example, a small cell lung carcinoma antigen (SCLCA).

For colorectal cancer (CRC) and/or locally advanced or metastatic head and/or neck cancer, a specific marker or markers may be selected from cell surface markers such as, for example, epidermal growth factor receptor (EGFR). For Duke's colorectal cancer (CRC) and its metastases, a specific marker or markers may be selected from cell surface markers such as, for example, Ep-CAM antigen.

For non-Hodgkin's lymphoma (NHL) and its metastases, a specific marker or markers may be selected from cell surface markers such as, for example, cluster designation/differentiation (CD) 20 antigen or CD22 antigen. For B-cell chronic lymphocytic leukemia and associated metastases, a specific marker or markers may be selected from cell surface markers such as, for example, CD52 antigen. For acute myelogenous leukemia and its metastases, a specific marker or markers may be selected from cell surface markers such as, for example, CD33 antigen.

For prostate cancers and their metastases, a specific marker or markers may be selected from cell surface markers such as, for example, prostate membrane specific antigen (PMSA). For carcinomatous meningitis and their metastases, a specific marker or markers may be selected from cell surface markers such as, for example, one of a vascular endothelial growth factor receptor (VEGFR) or an epithelial associated glycoprotein, for example, HMFGI (human milk fat globulin) antigen.

For lung, ovarian, colon, and melanoma cancers and their metastases, a specific marker or markers may be selected from cell surface markers such as, for example, B7-H1 protein. For colon, breast, lung, stomach, cervix, and uterine cancers and their metastases, a specific marker or markers may be selected from cell surface markers such as, for example, TRAIL Receptor-1 protein, a member of the tumor necrosis factor receptor family of proteins. For ovarian, pancreatic, non-small cell lung, breast, and head and neck cancers and their metastases, a specific marker or markers may be selected from cell surface markers such as, for example, EGFR (epidermal growth factor receptor).

For anti-angiogenesis targeting of tumor blood supply, a specific marker or markers may be selected from cell surface markers such as, for example, Integrin $\alpha v \beta 3$, a cell surface marker specific to endothelial cells of growing blood vessels.

For targeting of colon and bladder cancer and their metastases, a specific marker or markers may be selected from cell surface markers such as, for example, RAS, a signaling molecule that transmits signals from the external environment to the nucleus. A mutated form of RAS is found in many cancers.

The cell comprising the target may express several types of markers. One or more nanoparticles may attach to the cell via a ligand. The nanoparticle may be designed such it remains externally on the cell or may be internalized into the cell comprising the target. Once bound to the cell, the magnetic nanoparticle heats in response to the energy absorbed. For example, the magnetic nanoparticle may heat through hysteresis losses in response to an AMF. The heat may pass through the coating or through interstitial regions to the cell, for example via convection, conduction, radiation, or any combination of these heat transfer mechanisms. The heated cell becomes damaged, preferably in a manner that causes irreparable damage. When a sufficient amount of energy is transferred by the nanoparticle to the cell, the cell dies via necrosis, apoptosis or another mechanism.

The nanoparticles may comprise one or more ligands that target and attach to a biological marker. Suitable ligands for use herein include, but are not limited to, proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, and imprinted polymers and the like. The preferred protein ligands include, for example, cell surface proteins, membrane proteins, proteoglycans, glycoproteins, peptides and the like. The preferred nucleotide ligands include, for example, complete nucleotides, complimentary nucleotides, and nucleotide fragments. The preferred lipid ligands include, for example, phospholipids, glycolipids, and the like.

Covalent bonding may be achieved with a linker molecule. Examples of functional groups used in linking reactions include amines, sulfhydryls, carbohydrates, carboxyls, hydroxyls and the like. The linking agent may be a homobifunctional or heterobifunctional crosslinking reagent, for example, carbodiimides, sulfo-NHS esters linkers and the like. The linking agent may also be an aldehyde crosslinking reagent such as glutaraldehyde.

In an embodiment, the ligand may target one or more markers on a cancer cell. In another embodiment, the ligand may target a predetermined target associated with a disease of the patient's immune system. The particular target and one or more ligands may be specific to, but not limited to, the type of the immune disease. The ligand may have an affinity for a cell marker or markers of interest. The marker or markers may be selected such that they represent a viable target on T cells or B cells of the patient's immune system. The ligand may have an affinity for a target associated with a disease of the patient's immune system such as, for example, a protein, a cytokine, a chemokine, an infectious organism, and the like. For rheumatoid arthritis, a specific marker or markers may be selected from cell surface markers, such as, for example, one of CD52 antigen, tumor necrosis factor (TNF), and CD25 antigen. For rheumatoid arthritis and/or vasculitis, a specific marker or markers may be selected from cell surface markers such as, for example, CD4 antigen. For vasculitis, a specific marker or markers may be selected from cell surface markers such as, for example, CD18 antigen. For multiple sclerosis, a specific marker or markers may be selected from cell surface markers such as, for example, CD52 antigen.

In still another embodiment, the ligand targets a predetermined target associated with a pathogen-borne condition. The particular target and ligand may be specific to, but not limited to, the type of the pathogen-borne condition. A pathogen is defined as any disease-producing agent such as, for example, a bacterium, a virus, a microorganism, a fungus, and a parasite. For a pathogen-borne condition, the ligand for therapy utilizing nanoparticles may be selected to target the pathogen itself. For a bacterial condition, a predetermined target may be the bacteria itself, for example, one of *Escherichia coli* or *Bacillus anthracis*. For a viral condition, a predetermined target may be the virus itself, for example, one of Cytomegalovirus (CMV), Epstein-Barr virus (EBV), a hepatitis virus, such as Hepatitis B virus, human immunodeficiency virus, such as HIV, HIV-1, or HIV-2, or a herpes virus, such as Herpes virus 6. For a parasitic condition, a predetermined target may be the parasite itself, for example, one of *Trypanasoma cruzi*, Kinetoplastid, *Schistosoma mansoni, Schistosoma japonicum* or *Schistosoma brucei*. For a fungal condition, a predetermined target may be the fungus itself, for example, one of *Aspergillus, Cryptococcus neoformans* or *Rhizomucor*.

In another embodiment, the ligand targets a predetermined target associated with an undesirable target material. The particular target and ligand may be specific to, but not limited to, the type of the undesirable target. An undesirable target is a target that may be an undesirable material. Undesirable material is material associated with a disease or an undesirable condition, but which may also be present in a normal condition. For example, the undesirable material may be present at elevated concentrations or otherwise be altered in the disease or undesirable state. The ligand may have an affinity for the undesirable target or for biological molecular pathways related to the undesirable target. The ligand may have an affinity for a cell marker or markers associated with the undesirable target material. For arteriosclerosis, a predetermined target may be, for example, apolipoprotein B on low density lipoprotein (LDL). An undesirable material may be adipose tissue or cellulite for obesity, associated with obesity, or a precursor to obesity. A predetermined marker or markers for obesity may be selected from cell surface markers such as, for example, one of gastric inhibitory polypeptide receptor and CD36 antigen. Another undesirable predetermined target may be clotted blood.

In another embodiment, the ligand targets a predetermined target associated with a reaction to an organ transplanted into the patient. The particular target and ligand may be specific to, but not limited to, the type of organ transplant. The ligand may have an affinity for a biological molecule associated with a reaction to an organ transplant. The ligand may have an affinity for a cell marker or markers associated with a reaction to an organ transplant. The marker or markers may be selected such that they represent a viable target on T cells or B cells of the patient's immune system.

In another embodiment, the ligand targets a predetermined target associated with a toxin in the patient. A toxin is defined as any poison produced by an organism including, but not limited to, bacterial toxins, plant toxins, insect toxin, animal toxins, and man-made toxins. The particular target and ligand may be specific to, but not limited to, the type of toxin. The ligand may have an affinity for the toxin or a biological molecule associated with a reaction to the toxin. The ligand may have an affinity for a cell marker or markers associated with a reaction to the toxin. A bacterial toxin target may be, for example, one of Cholera toxin, Diphtheria toxin, and *Clostridium* botulinus toxin. An insect toxin may be, for example, bee venom. An animal toxin may be, for example, snake toxin, for example, *Crotalus durissus terrificus* venom.

In another embodiment, the ligand targets a predetermined target associated with a hormone-related disease. The particular target and ligand may be specific to, but not limited to, a particular hormone disease. The ligand may have an affinity for a hormone or a biological molecule associated with the hormone pathway. The ligand may have an affinity for a cell marker or markers associated with the hormone disease. For estrogen-related disease or conditions, a predetermined target may be, for example, estrogen or cell surface marker or markers such as, for example, estrogen receptor. For human growth hormone disease, the predetermined target may be, for example, human growth hormone.

In another embodiment, the ligand targets a predetermined target associated with non-cancerous disease material. The particular target and ligand may be specific to, but not limited to, a particular non-cancerous disease material. The ligand may have an affinity for a biological molecule associated with the non-cancerous disease material. The ligand may have an affinity for a cell marker or markers associated with the non-cancerous disease material. For Alzheimer's disease, a predetermined target may be, for example, amyloid B protein and its deposits, or apolipoprotein and its deposits.

In another embodiment, the ligand targets a proteinaceous pathogen. As an example, for prion diseases also known as transmissible spongiform encephalopathies, a predetermined target may be, for example, Prion protein 3F4.

In an embodiment, the nanoparticle is targeted to a cancer cell. In another embodiment, the particles will localize to a tumor, such as a metastatic tumor or micrometastases. Types of cancers include, but are not limited to, bladder, lung, breast, melanoma, colon, rectal, non-Hodgkin lymphoma, endometrial, pancreatic, kidney, prostate, leukemia, thyroid, and the like.

IV. DEFINITIONS

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

By "disease" or "cell disorder", it is meant any condition, dysfunction, or disorder that damages or interferes with the normal function of a cell, tissue, or organ.

The term "AMF" (an abbreviation for alternating magnetic field), as used herein, refers to a magnetic field that changes the direction of its field vector periodically, typically in a sinusoidal, triangular, rectangular or similar shape pattern, with a frequency of in the range of from about 80 kHz to about 800 kHz. The AMF may also be added to a static magnetic field, such that only the AMF component of the resulting magnetic field vector changes direction. It will be appreciated that an alternating magnetic field is accompanied by an alternating electric field and is electromagnetic in nature.

The term "coating", as used herein, refers to a material, combination of materials, or covering of the magnetic nanoparticle, comprising a suitable biocompatible material that serves to affect in vivo transport of the nanoparticle throughout the patient, and facilitates uptake and retention by diseased tissues and cell.

In some embodiments, the term "nanoparticle", as used herein, refers to a targeted nanoparticle that may comprise a magnetic nanoparticle core, coating, linker, and targeting ligand, that is used to selectively treat tissue by heating in response to an alternating magnetic field (AMF). Additionally, the nanoparticle may comprise a radioactive source or species that may become radioactive when exposed to an appropriate energy source. The nanoparticle may also comprise a chemotherapeutic agent, such as doxorubicin. In some embodiments, a nanoparticle comprises a coating, is attached to a target (such as a cell) by one or more targeting ligands.

The term "cell disorder" or "diseased tissue", as used herein, refers to tissue or cells associated with cancer of any type, such as bone marrow, lung, vascular, neuro, colon, ovarian, breast and prostate cancer; diseases of the immune system, such as AIDS; pathogen-borne diseases, which can be bacterial, viral, parasitic, or fungal, examples of pathogen-borne diseases include HIV, tuberculosis and malaria; hormone-related diseases, such as obesity; vascular system diseases; central nervous system diseases, such as multiple sclerosis; and undesirable matter, such as adverse angiogenesis, restenosis, amyloidosis, toxins, reaction-by-products associated with organ transplants, and other abnormal cell or tissue growth. The term "ligand", as used herein, refers to a molecule or compound that attaches to a nanoparticle and targets and attaches to a biological marker.

The terms "linker" or "linker molecule," as used herein, refer to an agent that targets particular functional groups on a ligand and on a magnetic particle or a coating, and thus forms a covalent link between any two of these.

The term "target", as used herein, refers to the matter for which deactivation, rupture, disruption or destruction is desired, such as a diseased cell, a pathogen, or other undesirable matter. A marker may be attached to the target.

By "contacting", it is meant any action that results in at least one molecule of one of the presently disclosed nano- or micro-particles physically contacting at least one cell. It thus may comprise exposing the cell(s) to the particle in an amount sufficient to result in contact of at least one particle with at least one cell. The method can be practiced in vitro or ex vivo, by introducing, and preferably mixing, the compound and cells in a controlled environment, such as a culture dish or tube. The method can be practiced in vivo, in which case contacting means exposing at least one cell in a subject to at least one particle of the presently disclosed subject matter, such as administering the particle to a subject via any suitable route. The method for administration of a magnetic material composition to a subject may include intraperitoneal injection, intravascular injection, intramuscular injection, subcutaneous injection, topical, inhalation, ingestion, rectal insertion, wash, lavage, rinse, or extracorporeal administration into a patient's bodily materials. According to the presently disclosed subject matter, contacting may comprise introducing, exposing, and the like, the particle at a site distant to the cells to be contacted, and allowing the bodily functions of the subject, or natural (e.g., diffusion) or man-induced (e.g., swirling) movements of fluids to result in contact of the particle and cell(s).

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

The "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the composition of the encapsulating matrix, the target tissue, and the like.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Materials and Methods for Preparation of Iron Oxide Nanoparticles

Anhydrous iron(III) chloride ($FeCl_3$) and anhydrous citric acid were purchased from GCE laboratory chemicals. Iron (II) chloride tetrahydrate ($FeCl_2.4H_2O$) and ammonia solution (25%) were purchased from Uni Chem Chemical and Merck Co (Whitehouse Station, N.J.), respectively. All the solvents and reagents were of analytical grade and used without further purification.

Magnetite ($Fe_3O_4$) particles were prepared in a small scale HGCP platform via co-precipitation method. Iron precursor solution was freshly prepared by 24.4 g of anhydrous $FeCl_3$ and 14.9 g of $FeCl_2.4H_2O$ in 500 mL of 0.74 M hydrochloric acid and kept under inert gas protection at 90° C. Under continuous flow of nitrogen gas, excess 25% ammonia solution was added with vigorous stirring. The reaction mixture turned black immediately and 40 mL of 0.2.4 M citric acid solution was added. Reaction was continued for 1 hour and magnetite particles were allowed to settle. The supernatant was decanted and settlement was isolated by centrifugation. The particles were washed several times by solvent/anti-solvent precipitation with water and acetone to achieve dispersion at pH 6-8. The trace of acetone was removed under reduced pressure at 60° C., for 15 minutes before the dispersion were treated hydrothermally at 130° C. for 5 hours. The final dispersion was placed under ultrasonic to ensure well dispersion. The final products were purged by argon gas and kept in a sealed bottle to prevent oxidation of $Fe_3O_4$ to $Fe_2O_3$.

Particle Size Analysis by DLS

The hydrodynamic diameter of the $Fe_3O_4$ was measured by a Horiba LB-550 Dynamic Light Scattering Particle Size distribution Analyzer with 0.01 wt Iron Oxide aqueous suspension. The distribution base was set to volume mode and the Refractive Index of $Fe_3O_4$ and deionized water (DI) water were set at 2.42 and 1.33, respectively.

Transmission Electron Microscope (TEM) and Scanning Electron Microscope (SEM)

The TEM image was acquired on a 200 kV JEOL 2010 transmission electron microscope. The specimen was prepared by placing a drop of suspension containing a drop of aqueous $Fe_3O_4$ (3 mass %) in 20 mL methanol onto a carbon coated copper grid followed by drying at room temperature for 24 hours. The size and morphology of the samples were also investigated with a KYKY-2800B scanning electron microscope (SEM).

X-Ray Diffraction (XRD) Analysis

The crystal structure and the phase purity and size of the samples were examined by X-ray powder diffraction (XRD) on a Philips expert diffractometer with Cu Kα radiation at room temperature. XRD was performed on powdered samples over the 2θ range of 28° to 67° with a step width of 0.1° and a sampling time of 4 seconds.

Thermal Gravimetric Analyzer (TGA)

The amount of surfactant coating on the $Fe_3O_4$ particles was examined on a thermal gravimetric analyzer (TGA), TA instrument 2050. Heating range was 25° C. to 800° C. under a nitrogen atmosphere with a heating rate of 20° C./min.

Iron Concentration Measurement by ICP-AES

The final concentration of $Fe_3O_4$ in the aqueous suspension was determined by a dual-view Optima 5300 DV TCP-AES (Inductively Coupled Plasma Atomic Emission spectroscopy) system in the Elemental Analysis Laboratory (EAL), Department of Chemistry, National University of Singapore (NUS), Singapore. The sample digestion and preparation were also performed at EAL based on the Milestone microwave laboratory system.

Specific Absorption Rate (SAR)

The SAR measurements were performed by the Department of Radiation Oncology & Molecular Radiation Sciences at Johns Hopkins University, (Baltimore, Md.).

Example 2

Characterization of Iron Oxide Nanoparticles

A representative schematic of high gravity controlled precipitation (HGCP) production of particles is shown in FIG. 1A. X-Ray powder diffraction (XRD) analysis confirmed the formation of $Fe_3O_4$ (FIG. 1B). Six characteristic peaks for $Fe_3O_4$ (2θ=30.3, 35.6, 43.3, 53.7, 57.3 and 62.9) as reported were observed.

The as-synthesized surface modified $Fe_3O_4$ particles were observed by SEM and TEM (FIG. 2). Both SEM and TEM images shown in FIGS. 2A and 2B, respectively, reveal that the single particle size of these $Fe_3O_4$ particles is around 20 nm and the TEM image shows that these particles have off-cubic morphology. The distinct ring pattern of the electron diffraction pattern shown in FIG. 2C signifies that the synthesized $Fe_3O_4$ is of high degree of crystallinity.

The surface modified $Fe_3O_4$ nanoparticles dispersed well in DI water and remained stable for more than 6 months with a mean hydrodynamic particle size of around 60 nm. The representative particle size distribution determined using dynamic light scattering is shown in FIG. 3A.

The amount of surfactants coating on the particle was monitored by TGA which revealed a total weight loss of 5% as shown in FIG. 3B. There was approximately 1.5% weight loss in the stage of 50~150° C. followed by another 3.5% loss in the stage of 200~50° C. and remained almost constant after 400° C. The first loss was caused by dehydration of the surface moisture while the latter was caused by the decomposition of the coated biocompatibie acid. The $Fe_3O_4$ particles contained around 95% magnetite on a mass basis.

IR spectra were recorded on an IR Prestige-21 spectrometer (SHIMADZU, Columbia, Md.; 400-4000 $cm^{-1}$ KBr pellets). The IR spectra of citric acid coated $Fe_3O_4$, pure $Fe_3O_4$, and pure citric acid are shown as curves a, b and c in FIG. 3C. Comparing the curves, the appearance of the characteristic absorption peaks at 590 $cm^{-1}$ curve a, which indicates the presence of $Fe_3O_4$. While the absorption of free citric acid at around $1700^{-1}$ to 750 $cm^{-1}$ (C=O) is not found in curve a, the absorptions at 1589.9 and 1396.9 $cm^{-1}$ are assigned as the stretching vibration of COO group of the citrate coated $Fe_3O_4$.

Three batches of citric acid coated $Fe_3O_4$ with mean size around 60 nm were prepared as described. The SAR (Specific Absorption Rate) plots showed that these particles were around 114 W/g Fe at magnetic field and frequency at 253 Oersteds and 150 kHz, respectively. The SAR plots in FIG. 4 demonstrate the reproducibility of the synthesis of the $Fe_3O_4$ particles with consistent SAR performance. In addition, no significant changes were observed in the SAR performance when the SAR of one of these samples was retested after 2 months.

The prepared nanoparticles were internalized by human prostate cancer cells (PC3 and Du145) for demonstration (FIG. 5A). Exposure to particles did not produce significant cytotoxicity, except for high concentrations of particle exposure (FIG. 5B). Exposure of Du145 cancer cells to citrate-coated particles in both low and high serum media (bovine serum albumin, BSA) demonstrated slightly increased tendency to internalize particles when cells were conditioned by low serum media, suggesting increased cell-particle interactions. Protein in media are hypothesized to form a "corona" on the particles upon contact with media that can influence cell-particle interactions. Thus, particle coating for biocompatibility and blood circulation following intravenous delivery may be an important consideration for systemic delivery of molecular targeted nanoparticles for non-invasive therapy.

Nanoparticles directly injected into Du145 (human prostate) subcutaneous thigh xenografts in mice will produce substantial heat within the tumor when exposed to AMF. By contrast, the measured rectal temperature of the same mouse (a surrogate measure of body core temperature) during treatment does not rise substantially, demonstrating the effective and localized deposition of heat by nanoparticles (FIG. 6). Histologic analysis from sectioned and excised tumors shows viable cells with injection of saline (phosphate buffered saline, no nanoparticles) and AMF (FIG. 7A), Also, tumor cells are viable when injected with nanoparticle formulation and no AMF (FIG. 73). When both nanoparticles and AMF are combined in the tumor following intra-tumor delivery, widespread necrosis (cell death) is observed in the vicinity of the nanoparticles (FIG. 7C). Cell death is localized to nanoparticle distribution, as demonstrated by cell viability for regions of tumor not containing nanoparticles as demonstrated by intact nuclei and cell membranes in FIG. 7C.

$Fe_3O_4$ nanoparticles aqueous dispersion with mean hydrodynamic particle size of around 60 nm and SAR of around 114 Wig Fe at magnetic field and frequency at 253 Oersteds and 150 kHz, respectively were prepared successfully.

Example 3

Materials and Methods for In Vitro and In Vivo Experiments

Rectangular Induction Coil for Cell Culture Experiments

The design of rectangular induction coil used in the study is described elsewhere (Nemkov et al., 2011). Briefly, the inductor consists of two single turn (square) copper tubes connected in parallel. At the ends of the copper tubes, copper blocks are connected to prevent the magnetic field from diverging at the ends of the coil. Fluxtrol 75 (Fluxtrol Inc., Auburn Hills, Mich.) is used as a magnetic core and is placed in the area inside of the tubes and over the upper edge of the tube. A water-cooled copper plate is placed on the outside of the cores to extract heat from the magnetic core generated during operation. A picture of the induction coil developed for heating the multi-well plates is shown in FIG. 8.

Field Mapping

The distribution of the magnetic field was measured using a magnetic field probe (AMF Life Systems, LLC, Rochester, Mich.), shown in FIG. 8B, and methods previously described (Bordelon et al., 2012). Magnetic field measurements were taken at the central height between the turns. Measurements were taken at multiple locations along the centerline. Five measurements were made in the coil length at 3.5, 7, 10.5, 14 and 17.5 cm from the copper plates at the start of the coil head. In the coil width, fifteen measurements were taken. One measurement every cm left and right from the centerline for 7 cm. The measurements were repeated 4 times and the results were averaged.

Thermal Management

Several thermal management methods were utilized to maintain a safe coil operating temperature and to shield cell culture samples from environmental temperatures in excess of 39° C. Nemkov et al., 2011 have described the design criteria and approaches for thermal management. Briefly, heat extraction through water cooling, concentrator material selection/orientation for reduced losses and better heat transfer, reduction of magnetic flux density by design modification, selection of proper materials for adhesion, and intermediate layers were utilized. Thermal load management during AMF system operation required for the rectangular coil h described previously (Nemkov et al., 2011). Initial testing of the coil was performed at a power supply voltage of 500 V, which led to an inductor voltage of 480 V. At this voltage the mean field strength along the center was 22.6 kA/m at 155 kHz. Proportionally for 31.8 kA/m at 150 kHz, 654 V will be needed in the coil head, a value close to the 650 V predicted by simulation. Thermal measurements were taken of the coil as well. The hottest surfaces of the inductor were in the same areas as predicted by simulation (Nemkov et al., 2011). The effectiveness of the cooling plates/recirculator system was tested by monitoring the temperature on the surface of the bottom cooling plate using fiber optic probes (FISO Technologies, Quebec, Canada). Measurement of the temperature on the bottom plate is most relevant as it is in the closest contact with the sample.

Iron-Oxide Nanoparticles (IONPs) Two commercially available IONPs were chosen to compare in-vitro heating characteristics with the newly developed particles.

Bionized NanoFerrite (BNF) and Nanomag-D-Spio Particles

Suspensions of starch-coated magnetite ($Fe_3O_4$) core-shell particles BNF-Starch (catalog no. 10-00-102) and nanomag-D-spio (catalog no. 79-00-102) were obtained from micromod Partikeltechnologie, GmbH (Rostock, Germany). Synthesis procedure and structural, heating and magnetic properties of these particles have been previously described (Gruettner et al., 2007; Gruttner et al., 1997; Dennis et al., 2009). Particle size of approximately 100 nm and AMF amplitude dependent heating characteristics are reported elsewhere (Bordelon et al., 2011).

JHU-MION (Newly Developed Particles)

Suspension of dextran-coated JHU iron oxide core-shell particles were prepared by Micromod Partikeltechnologie, GmbH (Rostock, Germany). The iron oxide core was prepared separately using a proprietary high-gravity controlled precipitation (HGCP) method (Nanomaterials Technologies, Ltd., Singapore) from aqueous solutions of precursor $FeCl_2$ and $NH_4OH$. Detailed description of synthesis and particle structure and magnetic characterization are in preparation for publication. The JHU-MION iron oxide cores were dextran coated using methods similar to those described for BNF particles (Gruettner et al., 2007) and was used as received. Size (~100 nm) and stability of the dextran-JHU-MION particles were tested. FIG. 2A shows a scanning electron microscope (SEM) image of the JHU-MIONs.

In Vitro Experiments

About 10,000 DU145 prostate cancer cells were added per well of two 48-well culture plates and allowed to grow in RPMI1640 without phenol red media (Invitrogen, Carlsbad, Calif.) containing 10% fetal bovine serum for 4 days at 37° C. and 5% CO2. Just prior to AMF treatment the indicated iron oxide nanoparticles were added in triplicates to the final concentrations of: 0.5, 1, 2, and 3 mg/mL Fe per well. 12 wells contained only cells and media to serve as control (FIG. 9). One of the two identical plates was subjected to AMF treatment in the coil described above. The second culture plate was used to characterize the cytotoxity from the particles alone.

Temperature Measurements

To monitor the change in temperature, 4 FISO RF-resistant fiber optic temperature probes (FISO, Inc., Quebec, Canada) were taped to the bottom of the plate under the wells containing the highest iron concentration (one for each particle and one for the control). In short, the coil geometry/dimensions make it impossible to fully insert an optical fiber temperature probe into the media without breaking the probe. To overcome this, "surrogate" temperatures were measured at the bottom surface of the plate under representative wells. This method or configuration provides reasonably accurate relative measure of temperature and heating for comparisons among the wells. It, however fails to provide an "absolute" measure of the temperature in the system. It is assumed that the temperature in all wells (before AMF heating, and in no particle controls) begins at the same value which is determined by the temperature set point (37° C.) of the water-jacket thermal management system. For each experiment, the culture plate was allowed to equilibrate with the coil for ~15 min prior to application of AMF. AMF was applied at 500V for 30 minutes.

Viability Assay

After the treatment, the plates were washed twice with the same growth media and kept at 37° C. and 5% CO2 for additional 4 days. The viability was assessed by neutral red uptake assay as described (Repetto et al., 2008). The neutral red assay is based on the ability of viable cells to incorporate and bind the neutral red dye which is slightly cationic. Neutral red is retained in the lysosomes of live and undamaged cells and can be extracted by a neutral destaining solution (49% ethanol, 1% glacial acetic acid in deionized water; Repetto et al., 2008). Briefly, 200 µL of cleared 40 µg/mL solution of neutral red (Sigma-Aldrich N4638, St. Louis, Mo.) was added to each well. After incubation at 37° C. for 3 hours, the neutral red medium was removed and the wells were washed with phosphate buffered saline. Neutral red destain solution was added (300 µL per well) and the plate was then placed on a shaker for about 20 min. Optical density (@450 nm) was measured by microplate reader spectrometer (SpectraMax M5, Molecular Devices, Sunnyvale, Calif.).

Animal Model

One 5-7 week old male nude mouse (Hsd: Athymic Nude-Foxn1$^{nu}$, Harlan Labs, Indianapolis, Ind.) weighing ~20 g prior to the treatment was used in this study. Male nude mice were selected for their relevance to our ongoing studies on prostate cancer therapy. The experiments were conducted using protocols approved by the Johns Hopkins Institutional Animal Care and Use Committee (Baltimore, Md.). Xenograft tumors were obtained by injecting $1\times10^6$ DU145 cells subcutaneously in the flank of male athymic nude mouse. Once the tumor reached to the size of about $0.15\pm0.02$ cm$^3$, IONPs were directly injected into the tumor.

Alternating Magnetic Field (AMF) System

In some embodiments, a high-throughput device capable of accommodating multi-well dishes is provided. Further, such a device must provide temperature control that is suitable for cell culture experiments (within physiologic limits) with continuous duty operation for more than one hour. This will ensure that the only heat stress on the cells originates from the nanoparticles and not from thermal losses of the device. The inductor needs to sustain low temperatures not only for the reliability of data but also to prevent degradation of the inductor for a long life cycle.

To address these requirements, a rectangular, modified Helmholtz coil that produces a homogeneous flux density AMF (<10% variation) throughout a volume having dimensions 86 mm×127 mm×19 mm with area sufficient to accommodate larger culture dishes (80 mm×120 mm), including a standard 96-well plate, was developed. The coil developed for this purpose has been previously described and characterized (Nemkov et al., 2011).

More particularly, the AMF system used for the in-vivo experiments has been described elsewhere (Kumar et al., 2013). A brief description is provided here. The AMF system comprises three main components: (a) the power source; (b) an external impedance matching (capacitance) network; and, (c) the load. The load comprises an inductor, or solenoid coil.

Results obtained using this coil with cell cultures containing multiple nanoparticle formulations for comparison are provided herein. Results obtained from hyperthermia experiments using the new IONP (JHU-MIONs) formulation in both cell culture (with modified Helmholtz coil) and mouse experiments are presented. The JHU-MIONs have higher heating capability at low H-values (<30 KA/m) compared to commercially available bionized-nanoferrite (BNFs).

The power source, matching network, and inductor were cooled with an industrial (80 kW rated) closed-loop circulating water/water cooling system comprising a 200-L reservoir of distilled water that is pumped through the RF system at a flow rate of 170 L/min and pressure 6 atm. The power supply was an 80-kW induction heating system manufactured by PPECO (Watsonville, Calif.) that provides an alternating current to a resonant circuit with variable frequency between 135 kHz and 440 kHz. The power supply (source) impedance was adjusted to match the coil and capacitance network by adjusting its internal inductance and capacitance. The external capacitance network (AMF Life Systems, Inc., Auburn Hills, Mich.) was adjusted for stable oscillation at 160±1 kHz.

Inductor or Solenoid Coil

For mNHP research, simple solenoids are typically used to perform experiments with small animal models and cancer cells in culture. While the solenoid geometry is adequate for small animal experiments, given the cylindrical shape of both coil and animal subject; this geometry is problematic for cell culture experiments. Few culture dishes are available that accommodate both necessary numbers of cells (>10,000) with a diameter sufficiently small to fit within the typical solenoid employed which often have a diameter less than 3 cm. Further, simple solenoid coils generate inhomogeneous fields necessitating precise sample positioning. To surmount these challenges, cell culture experiments are often performed by suspending the cells in a pellet form. While this is technically feasible, such experimental designs require additional manipulation of cells, and treatment in a state of suspension. These manipulations limit both the number of experimental samples that can be treated simultaneously and require many controls (Hedayati et al., 2013).

A four-turn solenoid with inner diameter of 45.5 mm, outer diameter of 57.5 mm, and a length of 32 mm was constructed from dehydrated annealed soft-copper refrigerator tubing having 6.4 mm outer diameter (OD). Measurements of the AMF amplitude were taken in the center of the coil with a magnetic field probe (AMF Life Systems, Inc., Auburn Hills, Mich.). The probe and methods used to map fields have been previously described (Bordelon et al., 2011; Bordelon et al., 2012). The field amplitude was measured in the coil center before each set of trials. The measured amplitude in this point is reported as the experimental amplitude.

Water Jacket

Custom built water is jacket described elsewhere (Kumar et al., 2013), briefly, water jacket was constructed from concentric poly-acrylic tubing filled with distilled water. To make the water cage device, two holes were drilled into the tube at opposite ends. Acrylic hose adapters were screwed into the holes with Teflon tape as a sealant. Water jacket inserted into the AMF coil can be seen in the FIG. 10. The water jacket helps anesthetized small animals to maintain the body temperature close to physiological range when exposed to AMF amplitudes ≤90 kA/m (Kumar et al., In Press).

Temperature Measurements

Anesthetized mouse was directly injected with JHU-MIONs. Intratumoral, rectal and contralateral skin temperatures were measured with three RF-resistant fiber optic temperature probes (FISO, Inc., Quebec, Canada). Animal with the fiber optic temperature probes was placed in a fashioned 50 mL conical tube and inserted into the water jacket. Temperatures were recorded at one-second intervals.

Example 4

Rectangular Induction Coil

Field Uniformity

AMF amplitude map from the measured data is shown in the FIG. 10. Field was found to be uniform (within ±10%) in 10 cm (x-axis)×14 cm (y-axis) area. The 48-well plate used in the study has outer dimensions of 8.6 cm×12.8 cm, lower surface area than the measured uniform field surface area. All the wells in the in-vitro experiments are exposed to uniform AMF amplitude. The results are displayed in the plot of FIG. 10 agrees very well with the modeling results previously reported (Nemkov et al., 2011).

Thermal Correction

The probes were initially immersed together in close contact in a warm water bath at a temperature close to the target temperature of the cooling plate. The temperatures were averaged over a stable time interval to identify offsets in their temperature measurements. The cooling plate temperature was then measured in the four quadrants of the plate at relevant voltage settings. The offset values were then subtracted from the recorded data to form corrected data.

Example 5

In Vitro Experiments

Temperature Measurements

Temperature data for control (cell only) and three IONPs (BNFs, SPIOs and JHU-MIONs) are shown in FIG. 11. Recorded temperatures showed significant heating due to JHU-MIONs compared to control (cell only), BNFs and SPIOs. For JHU-MIONs the recorded temperature showed a maximum temperature rise of ~7° C. while control, BNFs and SPIOs the temperature rise was ≤3° C.

Cell Viability

Consistent with temperature measurement data DU145 cells treated at higher concentrations JHU-MIONs (2-3 mg/mL Fe) show the lowest viabilities as compared to BNFs and SPIOs. Data shown in the FIG. 12 are normalized to the control without IONPs. Particles alone had no observable effect on the cell viability.

Example 6

In Vivo Experiments

FIG. 13 shows the temperature versus treatment time for intratumoral, contralateral and rectal temperatures. Intratumoral temperature rise of ~11° C. was observed. A net temperature rise of ~4° C. was observed in the rectal temperature.

Example 7

Discussion of In Vitro and In Vivo Experiments

Feasibility of using previously reported rectangular induction coil capable generating a uniform field (10 cm×14 cm) for in-vitro experiments was shown for the first time in this study. Recorded temperatures demonstrate JHU-MIONs heating ability compared to BNFs and SPIOs. Measured temperatures are relative measurements based upon comparison with controls, and do not represent absolute measures of temperature experienced by the cells. The measured temperatures provide a relative means to compare among particles. As result of the higher heat generated by the JHU-MIONs at low AMF amplitude (20 kA/m), the DU145 cell viability was found to be significantly reduced compared to BNFs (at 2-3 mg Fe/mL, FIG. 13).

During MNH, animals are anesthetized, whereupon the animals become hypothermic because normal thermoregulatory controls are temporarily compromised (Adair and Black, 2003; Black, 2006; Ivkov et al., 2005). Heat loss occurs through respiration and body surface cooling if ambient temperatures are significantly lower than the physiological norm. AMF deposits non-specific heat, potentially creating significant thermal gradients throughout the animal, which could be detrimental. During the initial phase of the MNH treatment, animal losses heat under the influence of anesthesia. After prolonged exposure to AMF additional heat is deposited in to the animal. If active and homogenizing temperature control can be provided during mNPH, safety may improve allowing increased limits on maximum allowable H-values (Kumar et al., 2013). Previous mouse studies suggest that rectal temperature change (ΔTRectal), should be maintained below 5° C., or below 42° C., for the safety of the animal (Ivkov et al., 2005). Here it is shown that in one embodiment, an ideal setting of 29 KA/m and ~4 mg Fe/g of tumor, AMF treatment yielded ΔTTumor >10° C. while maintaining the ΔTRectal <5° C. Both AMF amplitude and amount of iron injected are lower compared with 43.8 kA/m and 5 mg Fe/g of tumor used in Dennis et al., 2009 to achieve maximum ΔTTumor ~10° C.[9]. In the same study, three out of four animals with mean ΔTTumor ~15° C. (@55.7 kA/m and 5 mg Fe/g of tumor) showed complete regression of tumors after 15 min treatment. Considering low amounts of iron and AMF amplitudes used in this study JHU-MIONs have the potential to translate into a clinical product. Preclinical studies using JHU-MIONs are underway.

In the present study, the therapeutic relevant heating characteristics of the JHU-MIONs at low AMF amplitudes (20 kA/m) in an in-vitro set-up have been demonstrated. In-vivo feasibility test of JHU-MIONs demonstrated their ability to rise intratumoral temperature approximately 11° C. when injected with iron concentrations <4 mg Fe/g of tumor and exposed to an AMF amplitude of 29 kA/m. These preliminary studies provide motivation for further research and preclinical development of the JHU-MIONS.

Example 8

Materials and Measurement Methods for Amplitude-Dependent Effect Experiments

Particle size analysis by DLS, Transmission Electron Microscope (TEM) and Scanning Electron Microscope (SEM) methods, x-ray diffraction (XRD) analysis, iron concentration measurements by ICP-AES, and specific absorption rate measurements were performed as described in Example 1.

Mössbauer Spectroscopy

The composition of the samples was determined by $Fe^{57}$ Transmission Mossbauer spectroscopy using a constant acceleration spectrometer calibrated with α-Fe at room temperature and a 1 GBq $Co^{57}$ source. Spectra were collected with the samples in a Janis SHI-850 closed cycle refrigeration system (Janis Research Co., Wilmington, Mass.) at 10K.

Magnetometry

Hysteresis loops were measured at temperatures ranging between 300K to 5K from ±5570 kA/m (±70,000 Oe) using a Superconducting Quantum Interference Device Vibrating Sample Magnetometer (SQUID VSM) from Quantum Design, Inc. (San Diego, Calif.). The colloidal samples were loaded into Kel-F liquid capsules from LakeShore Cryogenics (Westerville, Ohio), and sealed with epoxy to prevent evaporation of the water solvent during measurement under vacuum.

SANS

Unpolarized SANS data taken with 0.84 nm wavelength neutrons in transmission using three detector settings in order to span the range of scattering vectors Q from $3 \times 10^{-5}$ to $5 \times 10^{-1}$ Å$^{-1}$.

For PASANS, to cover the necessary Q range of (0.005-0.2) Å$^{-1}$ for the BNFs, two different wavelengths of neutrons were used: (5±0.6) Å and (7.5±0.9) Å. The 5 Å (7.5 Å) neutrons were polarized with an efficiency of 0.888±0.005 (0.935±0.003) by scattering from an FeSi supermirror, sending the spin-up (+) neutrons down the beam line. Prior to interaction with the sample, the incident neutron polarization direction can be reversed at any time using an electromagnetic flipper coil with a flipping efficiency of 0.988±0.004 (0.979±0.003). [For the JHUs and SPIOs, only the (7.5±0.8) Å neutrons were used to cover the necessary Q range of (0.005-0.06) Å$^{-1}$. The 7.5 Å neutrons were polarized with an efficiency of 0.95±0.02 with the FeSi supermirror, and the electromagnetic flipper coil had a flipping efficiency of 0.975±0.009.] After scattering from the sample of interest, an analyzing glass cell filled with polarized $^3$He gas preferentially allows neutrons with spins aligned parallel to the $^3$He atoms to pass through, while absorbing neutrons of the other spin state. The orientation of the $^3$He spin filter can also be reversed at any time with a nuclear magnetic resonance pulse of an appropriate frequency. The data is then corrected for detector efficiency, background, and the polarization efficiency plus the time-dependence of the $^3$He cell according to previously described methods.

Example 9

Amplitude-Dependent Effect Experiments

With the development of new syntheses for controlling size, shape, and crystallinity of magnetic nanoparticles in the last two decades, new applications of magnetic nanoparticles have been developed. In particular, the biomedical applications of magnetic nanoparticles have been rapidly expanding from ex vivo diagnostic tools like cell-(Shao et al., 2012) and immuno-assays (Jin et al., 2009), to in vivo diagnostic tools like magnetic resonance imaging (MRI; Swierczewska et al., 2011) and magnetic particle imaging (MPI; Gleich and Weizenecker, 2005), as well as to therapeutic techniques such as hyperthermia (Lehmann et al., 2008) and drug delivery (Kim et al., 2008). However, in developing any particular nanoparticle system for a specific application, there is a complex interplay between the structure and the optimal magnetic properties. This interplay is significantly constrained once biocompatibility (composition, stability in blood, bio-distribution, etc.) are added.

In hyperthermia, these constraints are particularly evident. The magnetic nanoparticles must have a large enough moment to interact, but not so large that the magnetic attraction is stronger than steric/electrostatic repulsion; otherwise, the nanoparticles will agglomerate. The nanoparticles must also have a significant anisotropy present, but they cannot have an aspect ratio greater than approximately 3:1 or their circulation time in the bloodstream will be very short. The magnetic moment of the core material must be maximized, but they must also be stable under physiological conditions and biocompatible. These and other constraints leave a narrow window in which to design effective nanoparticles for hyperthermia.

Finally, the methodology itself also imposes constraints. In hyperthermia, the magnetic nanoparticles are subjected to an alternating magnetic field in order to deposit energy in the form of heat into the surrounding cancerous tissue. However, the amount of energy deposited, as quantified by specific absorption rate (SAR) or, more correctly, the specific loss power (SLP), is determined, in part, by the magnetic field amplitude. The magnetic field amplitude, in turn, is limited by the power generation requirements to produce a uniform field over for whole body vs. localized regions. Therefore, it is critical to understand the parameters important in determining how a given magnetic nanoparticle system responds to the magnetic field amplitude at fixed frequency. This is especially important, because most experimental systems only examine the SLP at one or two fields at fixed frequency. To date, no systematic studies have been performed that look at the behavior of a nanoparticle system as a function of field or frequency.

In this Example, the heat characteristics are examined of three different nanoparticle systems, which are all similar in size and composition, as a function of applied field at fixed frequency. After characterizing the nanoparticles both physically and magnetically, the parameters responsible for determining their heat generation are identified. In addition to the previously established importance of interactions (Dennis et al., 2009), it has been found that the internal structure of the magnetic nanoparticles plays a significant role in determining the SLP.

The first system, called Bionized Nano-Ferrite (BNFs), is synthesized by a high temperature, high pressure homogenization process (Gruettner et al., 2007). As determined by Mössbauer spectroscopy (FIG. 17), the resulting core is composed of 77% $Fe_3O_4$ and 18% $\gamma$-$Fe_2O_3$ with about 4% $Fe(OH)_2$. Unpolarized Small Angle Neutron Scattering (SANS) demonstrates that the core is composed of parallelepipeds approximately 8.8 nm×24 nm×96 nm (data not shown). Scherrer analysis from X-Ray Diffraction (XRD) confirms that the core is composed of grains which are (12±2) nm in size, on the order of the smallest dimension of the parallelepipeds (data not shown). The core is coated twice with a 40,000 Dalton dextran shell. Dynamic Light Scattering (DLS) indicates that the total particle diameter is 126 nm with a distribution ($\sigma$) of 39% (FIG. 14). Transmission Electron Microscopy (TEM) demonstrates that the iron oxide crystallites are ~20 nm, in agreement with SANS (data not shown). For the subsequent magnetometry and SANS measurements, unless otherwise indicated, the samples are measured in water at a particle (iron) concentration of 22 (11) mg/mL.

The second system, called JHU particles, is synthesized by a high-gravity controlled precipitation method. As determined by Mossbauer spectroscopy (FIG. 18), the resulting core is composed of 76% $Fe_3O_4$ and 24% $\gamma$-$Fe_2O_3$. Unpolarized SANS (data not shown) demonstrates that the core is composed of grains which are approximately spherical in shape and (8±3) nm in radius. Scherrer analysis from XRD (data not shown) confirms that the core is composed of grains which are (9±1) nm in size. The core is coated with a dextran shell, and DLS confirms a hydrodynamic diameter of 117 nm with a distribution ($\sigma$) of 41% (FIG. 15). TEM demonstrate that the iron oxide crystallites are ~15 nm, in agreement with SANS (data not shown). For the subsequent magnetometry and SANS measurements, unless otherwise indicated, the samples are measured in water at a particle (iron) concentration of 64 (9.2) mg/mL.

The third system, called Nanomag-SPIOs, is synthesized by a co-precipitation of iron salts in the presence of dextran (Rudershausen et al., 2002). As determined by Mossbauer spectroscopy (FIG. 19), the resulting nanocrystallites are composed of 87% $Fe_3O_4$ and 13% $\gamma$-$Fe_2O_3$. Unpolarized SANS (data not shown) demonstrates that the core is composed of grains which are approximately spherical in shape and, on average, 4.4 nm in radius. Scherrer analysis from XRD confirms that the nanocrystallites are composed of grains which are ~8 nm in size (data not shown). The nanocrystallites are embedded within a 40,000 Dalton dextran shell, and DLS confirms a hydrodynamic diameter of 106 nm with a distribution ($\sigma$) of 50% (FIG. 16). TEM demonstrate that the nanocrystallites are ~20 nm, demonstrating the presence of agglomeration of the grains (data not shown). For the subsequent magnetometry and SANS measurements, unless otherwise indicated, the samples are measured in water at a particle (iron) concentration of 96 (12.5) mg/mL.

The saturation magnetizations (MS) of the particles were measured at room temperature using SQUID magnetometry and normalized to the iron content for direct comparison with the SLP (FIG. 20). (For comparison with the literature, the saturation magnetization is also normalized to total particle mass, including dextran, and shown in brackets. Due to the inclusion of the mass of the dextran, these saturation values are significantly below that of the bulk.) For the BNFs, MS is the highest at (80.76±0.06) A-m2/kg [(19.86±0.02) A-m2/kg]. For the JHUs, MS=(73.6±0.1) A-m2/kg [(10.558±0.001) A-m2/kg]. For the SPIOs, MS is the lowest at (67.69±0.01) A-m2/kg [(8.814±0.001) A-m2/kg]. In summary, MS when normalized to iron content, only varies by 15% across the three samples. However, upon consideration of the region about zero field with realistic hyperthermia field amplitudes (±80 kA/m), there are small differences in the shape of the hysteresis loops (inset to FIG. 20). These can be most readily attributed to either interactions (Taketomi and Shull, 2002) in the sample or differences in the anisotropy (Poddar et al., 2008). The interactions can be probed by looking at the virgin curve and comparing it with the major loop. The BNFs exhibit strong interactions (shown by the deviations from the major loop), while the JHU particles have somewhat weaker interactions, and the SPIOs have very weak interactions. The anisotropy field (Hk) can be directly measured using transverse susceptibility (data not shown). (Due to signal to noise issues, these measurements are made at 5K.) For the BNFs, μ0Hk=10 mT. For the JHUs, μ0Hk=14 mT. Given that μ0Hk=2Keff/Ms, Keff=2.977(3)×10-7 J and 2.82(2)×10-7 J for the BNFs and JHUs, respectively. (Normalized to iron concentration, Keff=4.034(4)×10-4 J/kg of Fe and 5.11(4)× 10-4 J/kg of Fe for the BNFs and JHUs, respectively.) So, magnetically, the nanoparticles are all similar. Therefore, only small variations in the SLP are expected between the different samples. In contrast, there is a significant variation (FIG. 21) in the SLP of the samples, both in magnitude as well as onset and slope, as a function of the applied magnetic field. (The measurement frequency is fixed at 150 kHz.) The BNFs fail to generate significant heat until approximately 20 kA/m, and the SLP is still increasing past 500 W/g-Fe at 65 kA/m. The JHUs start to generate significant heat above approximately 5 kA/m, and then plateau at about 440 W/g-Fe at approximately 50 kA/m. The SPIOs plateau at about 150 W/g-Fe at approximately 30 kA/m. These significant variations, however, cannot originate from the minor differences seen so far. In particular, they cannot be accounted for simply by changes in the magnetization with field, as can be clearly demonstrated by considering the JHU and BNF nanoparticles above 50 kA/m. Here, when the JHUs are saturating in SLP, the DC hysteresis loop of the JHUs are overlapping with the BNFs, and both are still increasing. Therefore, there must be an additional factor which has not been accounted for yet.

In an AC magnetic field, such as is applied during hyperthermia, the moments have to very rapidly reorient themselves to align with the field. Therefore, the internal magnetic structure may play a critical role in both the mechanism of reorientation as well as the energy that must be provided for this reorientation. To explore the detailed internal magnetic structure, polarization analyzed small angle neutron scattering (PASANS) was used at room temperature on the nanoparticles in $D_2O$ under an applied guide magnetic field of 1.5 mT. (Unpolarized neutrons were not sufficient for determining the magnetic structure, since the magnetic signal is relatively weak when the nanoparticles are contrasted with $H_2O$, and the magnetic structure determination is ambiguous when the nanoparticles are contrasted with $D_2O$.) The SANS measurements were performed at the NIST Center for Neutron Research on the NG-3 beamline.

For the BNFs, to cover the necessary Q range of (0.005-0.2) Å$^{-1}$, two different wavelengths of neutrons were used: (5±0.6) Å and (7.5±0.9) Å. The 5 Å (7.5 Å) neutrons were polarized with an efficiency of 0.888±0.005 (0.935±0.003) by scattering from an FeSi supermirror, sending the spin-up (+) neutrons down the beam line. Prior to interaction with the sample, the incident neutron polarization direction can be reversed at any time using an electromagnetic flipper coil with a flipping efficiency of 0.988±0.004 (0.979±0.003). [For the JHUs and SPIOs, only the (7.5±0.8) A neutrons were used to cover the necessary Q range of (0.005-0.06) Å$^{-1}$. The 7.5 Å neutrons were polarized with an efficiency of 0.95±0.02 with the FeSi supermirror, and the electromagnetic flipper coil had a flipping efficiency of 0.975±0.009.] After scattering from the sample of interest, an analyzing glass cell filled with polarized 3He gas preferentially allows neutrons with spins aligned parallel to the 3He atoms to pass through, while absorbing neutrons of the other spin state. The orientation of the 3He spin filter can also be reversed at any time with a nuclear magnetic resonance pulse of an appropriate frequency. The data is then corrected for detector efficiency, background, and the polarization efficiency plus the time-dependence of the 3He cell according to previously described methods.

Starting with the neutron polarization spin state as + or −, measurement of all four neutron spin cross-sections (++, +−, −+, and −−) allows for the unique separation of nuclear scattering (N2) from magnetic scattering, irrespective of whether the sample is magnetically saturated. Simply, the "+ to +" and "− to −" scattering (or non-spin-flip scattering) contains information about primarily magnetic scattering from moments parallel to the applied sample field and nuclear scattering, while "+ to −" and "− to +" (or spin-flip scattering) contains only magnetic scattering. The complete, angle-dependent polarization selection rules simplify at several key angles and enable the unambiguous separation of the nuclear scattering (N2) from magnetic scattering of moments parallel to the applied guide field (M2Y=M2PARL) and those perpendicular to the applied field (M2PERP which is a linear combination of M2X and M2Z) for any field ≥1 mT. Starting from the efficiency-corrected 2D scattering patterns from the magnetite nanoparticles in the 1.5 mT field parallel to the Y axis, area-normalized sector slices of ±10o are taken about θ=0o, where θ is the angle between the X axis (horizontal midline of the detector) and the projection of Q onto the X-Y detector plane. At this specific angle, M2PERP=M2Z.

Once the three components, N2, M2PERP, and M2PARL, have been calculated, they can be fit to the appropriate model to (a) verify the nuclear structure determined previously with unpolarized SANS and (b) determine the magnetic domain sizes parallel and perpendicular to the applied magnetic field of 1.5 mT.

In terms of the BNFs, fitting N2 with the parallelepiped model results in 7 nm×33 nm×77 nm parallelepipeds which are similar to those determined from the unpolarized neutrons (FIG. 22). The magnetic scattering shows dramatically different sizes parallel and perpendicular to the applied magnetic field (FIG. 23). This data was fit with a parallelepiped model, but a spherical model also works as the fit is most sensitive to the smallest dimension. This results in a domain structure which is ~22 nm parallel to the field and ~8 nm perpendicular to the field, and is shown graphically in the inset to FIG. 23. As determined previously (Krycka et al., 2011), this magnetic domain structure does not necessarily align with the crystallographic grains. This break-up into domains is not unsurprising, although the core size is smaller than the nominal single domain size for magnetite. Furthermore, given the measured parameters, this structure is in agreement with micromagnetic simulations.

For the JHUs, N2 still fits nicely to the spherical model, with the same grain size as determined with the unpolarized beam (FIG. 22). The magnetic scattering also demonstrates a domain structure, but the average domain size is significantly larger than what is seen in the BNFs (FIG. 24). This data was fit with a spherical model, which results in a domain structure which is ~19 nm in radius parallel to the field and ~6 nm in radius perpendicular. These sizes indicates that, for a 50 nm core, the particles are magnetically more core/shell, where the core is 38 nm in diameter and magnetized parallel to the field, and the shell, of thickness 6 nm, is magnetized perpendicular to the field. This is shown graphically in the inset to FIG. 24.

For the SPIOs, N2 still fits nicely to the spherical model, with the same grain size (within error) as determined with the unpolarized beam (FIG. 22). In contrast, the magnetic scattering parallel to the field is barely above background (FIG. 25). Plots of the subtracted signal, an indication of the net moment, are so low that effectively there is no measureable magnetic moment. Therefore, it is reasonable to assume that the domain size parallel to the field is commensurate with the nuclear grain size. (It is possible to plot a curve through the M2PARL data based on this assumption.) The magnetic scattering perpendicular to the field is slightly better (FIG. 25), and clearly shows a domain size of 6 nm in radius, which is commensurate with the nuclear grain size. This domain structure is shown graphically in the inset to FIG. 25.

In summary, the BNFs have a high saturation magnetization, with a moment that breaks up into long slender domains. Without wishing to be bound to any one particular theory, it is believed that the 2% iron hydroxide component might be a thin surface coating on each parallelepiped that forms prior to the final core formation. (There is no known method of verifying absolutely that this is the case, because TEM does not have the resolution to identify the differences over a single monolayer.) However, this means that each domain will be strongly coupled to its neighbor. Therefore, a larger field must be applied to change that coupling and force all of the moments to align. This accounts for the higher field required before on-set of significant heating.

In contrast, the JHUs have a slightly lower saturation magnetization (by ~9%) than the BNFs, and break up into one or two large domains. The JHUs also have a larger anisotropy (by ~20%), perhaps controlled by the higher concentration of $\gamma$-$Fe_2O_3$, which in bulk has a ~50% larger anisotropy than that of $Fe_3O_4$. We also hypothesize that during formation, each grain starts out as $Fe_3O_4$, with the surface changing to $\gamma$-$Fe_2O_3$ during the high temperature phase. Eventually, these grains coalesce to form the final core, but the individual grains have an $Fe_3O_4$ core and $\gamma$-$Fe_2O_3$ shell. The nominal reduction in the saturation magnetization of bulk $\gamma$-$Fe_2O_3$ shell in combination with the change in anisotropy, could allow the grains to be less coupled together magnetically than the BNFs. This would result in a lower on-set of significant SLP, than the BNFs.

Finally, the lack of coherent moment present in the SPIOs means that all of the individual grains are weakly coupled, at best. Therefore, they have the lowest on-set of measurable SLP, because it is easier to magnetize each individual grain, since the total moment is being magnetized, and multiple domains do not have to be aligned. However, due to their weak interactions, they are not capable of producing nearly as much heat.

This means that when designing magnetic nanoparticles for hyperthermia, the internal magnetic structure and the exchange coupling between any domains must be taken into account as well as any coupling (interactions) between nanoparticles and the resulting anisotropy. This will allow for design of particles at a fixed frequency to maximize heating at lower fields for whole body or metastatic cancers versus being able to take advantage of higher fields and therefore higher SLP from localized cancers like neck and throat or prostate. However, it is expected that when changing the frequency, there will be optimal interaction strength both between particles and within a particle to maximize the heating. At higher frequencies, such as 1 MHz (Southern et al.), strong interactions will slow down the dynamic response of the particles, thereby requiring higher fields to flip the magnetization or resulting in lower SLP for a given field.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Adair, E. R., and Black, D. R., "Thermoregulatory responses to RF energy absorption," Bioelectromagnetics 6(Supplement), S17-S38 (2003);

Atkinson, W. J., Brezovich, I. A., Chakraborty, D. P., "Usable frequencies in hyperthermia with thermal seeds," IEEE Trans. Biomed. Eng. 31, 70-75 (1984);

Black, D. R., [Thermoregulation in the presence of radio frequency fields], Biological and Medical Aspects of Electromagnetic Fields, 3rd Edition, Boca Raton, 215-226 (2006);

Bordelon, D., et al. "Magnetic nanoparticle heating efficiency reveals magneto-structural differences when characterized with wide ranging and high amplitude alternating magnetic fields," Journal of Applied Physics 109, 12904.1-12904.8 (2011);

Bordelon, D., Goldstein, R., Nemkov, V., Kumar, A., Jackowski, J., DeWeese, T. L., Ivkov, R., "Modified solenoid coil that efficiently produces high amplitude AC magnetic fields with enhanced uniformity for biomedical applications," IEEE Trans. on Magnetics 48, 47-52 (2012);

Dennis C L, et al. "Nearly complete regression of tumors via collective behavior of magnetic nanoparticles in hyperthermia," Nanotechnology 20(39), Article Number 395103 (2009);

Dennis C. L., A. J. Jackson, J. A. Borchers, P. J. Hoopes, R. Strawbridge, A. R. Foreman, J. van Lierop, C. Grüttner, and R. Ivkov, Nanotechnology, 20 (2009) 395103;

Gruettner C, K. Mueller, J. Teller, F. Westphal, A. Foreman, and R. Ivkov, J. "Synthesis and antibody conjugation of magnetic nanoparticles with improved specific power absorption rates for alternating magnetic field cancer therapy," Journal of Magnetism and Magnetic Materials 311(1), 181-186 (2007);

C. Grüttner, J. Teller, W. Schütt, F. Westphal, C. Schümichen and B. R. Paulke, Preparation and Characterization of Magnetic Nanospheres for in vivo Application. In Scientific and Clinical Application of Magnetic Carriers (U. O. Hafeli, W. Schütt, J. Teller and M. Zborowski, Eds.), pp. 53-68. Plenum Press, New York, 1997;

Hedayati, M., Thomas, O., Abubaker-Sharif, B., Zhou, H., Cornejo, C., Zhang, Y., Wabler, M., Mihalic, J., Gruettner, C., Westphal, F., Geyh, A., Deweese, T. L., Ivkov, R., "The effect of cell cluster size on intracellular nanoparticle-mediated hyperthermia: is it possible to treat microscopic tumors?," Nanomedicine (Lond) 8(1), 29-41 (2013);

Ivkov, R., DeNardo, S. J., Daum, W., Foreman, A. R., Goldstein, R. C., Nemkov, V. S., DeNardo, G. L., "Application of high amplitude alternating magnetic fields for heat induction of nanoparticles localized in cancer," Clin. Cancer Res. 11(19 Suppl), 7093s-7103s (2005);

Jordan, A., Wust. P., Scholz, R., Faehling, H., Krause, J. and Felix, R., [Magnetic Fluid Hyperthermia (MFH)], Scientific and Clinical Applications of Magnetic Carriers, New York, 569-595 (1997);

Kim, J., J. E. Lee, S. H. Lee, J. H. Yu, J. H. Lee, T. G. Park, and T. Hyeon, Adv. Mater., 20 (2008) 478;

Krycka, K. L., A. J. Jackson, J. A. Borchers, J. Shih, R. Briber, R. Ivkov, C. Griittner, and C. L. Dennis, Journal of Applied Physics, 109 (2011) 07B513.

Kumar, A., Attaluri, A., Mallipudi, R, Cornejo, C., Bordelon, D., Armour, M., Morua, K., DeWeese, T. L., Ivkov, R., "Method to reduce non-specific tissue heating of small animals in solenoid coils," Int. J Hyperthermia, 29, 106-120 (2013); Nemkov V, et al. "Magnetic field generating inductor for cancer hyperthermia research," Compel 10(5), 1626-1636 (2011);

Poddar, P., M. B. Morales, N. A. Frey, S. A. Morrison, E. E. Carpenter, and H. Srikanth, J. Appl. Phys., 104 (2008);

Repetto G, et al. "Neutral red uptake assay for the estimation of cell viability/cytotoxicity," Nature Protocols 3(7), 1125-1131 (2008);

Rosensweig, R. E., "Heating magnetic fluid with alternating magnetic field," J. Magnetism and Magn. Materials 252, 370-374 (2002);

Rudershausen S, Grüttner C, Frank M, Teller J, Westphal F: Multifunctional Superparamagnetic Nanoparticles for Life Science Applications. European Cell and Materials 3, 81-83 (2002);

Southern, P., D. Ortega, C. Johansson, and Q. Pankhurst, Talk 35 of the 9th International Conference on the Scientific and Clinical Applications of Magnetic Carriers, Minneapolis, Minn.; and Taketomi, S. and R. D. Shull, J. Appl. Phys., 91 (2002) 8546-8548.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A magnetic nanoparticle comprising:
   (a) a magnetic core comprising an aggregate of at least two magnetic crystalline grains, wherein the aggregate exhibits a collective magnetic phase such that the core has an apparently single magnetic domain phase;
   (b) a second magnetic phase or magnetic oxide phase differing from the collective or single domain phase of the core, wherein the second magnetic phase or magnetic oxide phase can intercalate and surround the core; wherein at least one magnetic phase exhibits a "hard" or high-coercive behavior in a magnetic field and at least one other phase exhibits a "soft" or low-coercive behavior in a magnetic field relative to the "hard" magnetic phase; and
   (c) a coating.

2. The magnetic nanoparticle of claim 1, wherein the core substantially comprises $Fe_3O_4$ and the second magnetic phase or magnetic oxide phase substantially comprises $\gamma$-$Fe_2O_3$.

* * * * *